United States Patent
Gharavi et al.

(10) Patent No.: US 10,202,647 B2
(45) Date of Patent: Feb. 12, 2019

(54) MUTATIONS IN DSTYK CAUSE DOMINANT URINARY TRACT MALFORMATIONS

(71) Applicant: THE TRUSTEES OF COLUMBIA UNIVERSITY IN THE CITY OF NEW YORK, New York, NY (US)

(72) Inventors: Ali Gharavi, New York, NY (US); Simone Sanna-Cherchi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 168 days.

(21) Appl. No.: 14/783,078

(22) PCT Filed: Apr. 14, 2014

(86) PCT No.: PCT/US2014/034056
§ 371 (c)(1),
(2) Date: Oct. 7, 2015

(87) PCT Pub. No.: WO2014/169294
PCT Pub. Date: Oct. 16, 2014

(65) Prior Publication Data
US 2016/0040238 A1   Feb. 11, 2016

Related U.S. Application Data

(60) Provisional application No. 61/811,365, filed on Apr. 12, 2013.

(51) Int. Cl.
| | | |
|---|---|---|
| *C12N 15/113* | (2010.01) | |
| *C12Q 1/6883* | (2018.01) | |
| *C07K 16/40* | (2006.01) | |
| *G01N 33/573* | (2006.01) | |

(52) U.S. Cl.
CPC ............ *C12Q 1/6883* (2013.01); *C07K 16/40* (2013.01); *C12N 15/1137* (2013.01); *G01N 33/573* (2013.01); *C12N 2310/14* (2013.01); *C12N 2320/30* (2013.01); *C12Q 2600/156* (2013.01); *C12Q 2600/158* (2013.01); *C12Q 2600/16* (2013.01); *G01N 2333/91* (2013.01); *G01N 2333/912* (2013.01); *G01N 2800/34* (2013.01); *G01N 2800/347* (2013.01)

(58) Field of Classification Search
CPC ..................... C12N 15/113; A01K 2207/05
See application file for complete search history.

(56) References Cited

U.S. PATENT DOCUMENTS

| 5,139,932 A | 8/1992 | Cederholm et al. |
| 6,429,024 B1 | 8/2002 | Kokubo et al. |
| 6,962,984 B2 | 11/2005 | Ishiwata et al. |
| 7,521,190 B2 | 4/2009 | Jones et al. |
| 2008/0152659 A1 | 6/2008 | Hageman |
| 2009/0029908 A1 | 1/2009 | Mukherjee et al. |
| 2009/0258822 A1 | 10/2009 | Hageman |
| 2009/0312394 A1 | 12/2009 | Hughes |
| 2010/0009368 A1 | 1/2010 | Young |
| 2010/0297660 A1 | 11/2010 | Winkler et al. |
| 2011/0020810 A1 | 1/2011 | Winn et al. |
| 2011/0318738 A1 | 12/2011 | Jones et al. |

FOREIGN PATENT DOCUMENTS

| RU | 2269297 C1 | 2/2006 |
| WO | 98/32849 A2 | 7/1998 |
| WO | 1998032849 | 7/1998 |
| WO | 2003/000842 A2 | 1/2003 |
| WO | 2003000842 | 1/2003 |
| WO | 2010/038974 A2 | 4/2010 |

OTHER PUBLICATIONS

Peng et al. (Biochemica et Biophysica Acta 1759 (2006) 562-572).*
Zha et al Biochemical and Biophysical Research Communications 319 298-303 (Year: 2004).*
Peng et al. Biochim Biophys Acta. 2006 1759:562-572 (Year: 2006).*
Zha et al., "Homo sapiens Dual Serine/Threonine and Tyrosine Protein Kinasee (DSTYK), Transcript Variant 1, mRNA: RIP5 is a RIP-Homologous Inducer of Cell Death", Jun. 25, 2004, pp. 298-303, vol. 319, No. 2, Publisher: Biochem Biophys Res Commun, Published in: http://www.ncbi.nlm.nih.gov/sviewer/batchseq.cgi?noredirect=1&db=nuccore&val=NM_015375.2.
Song et al., "Genetics of Congenital Anomalies of the Kidney and Urinary Tract", 2011, pp. 353-364, vol. 26, Publisher: Pediatr Nephrol, Published in: http://www.ncbi.nlm.nih.gov/pubmed/20798957.
Sanna-Cherchi et al., "Renal Outcome in Patients With Congenital Anomalies of the Kidney and Urinary Tract", Jun. 17, 2009, pp. 528-533, vol. 76, Publisher: Kidney Intenational, Published in: http://www.ncbi.nlm.nih.gov/pubmed/19536081.
Rensing et al., "The Physcomitrella Genome Reveals Evolutionary Insights Into the Conquest of Land by Plants", May 22, 2009, pp. 64-69, vol. 319, No. 5859, Publisher: NCBI, Published in: http://www.ncbi.nlm.nih.gov/pubmed/18079367.

(Continued)

*Primary Examiner* — Brian A Whiteman
(74) *Attorney, Agent, or Firm* — Timothy van Dyke; Beusse Wolter Sanks & Maire

(57) ABSTRACT

Congenital abnormalities of the kidney or the urinary tract (CAKUT) are the most common cause of pediatric kidney failure. These disorders are highly heterogenous, and their etiology is poorly understood. Dual serine/threonine and tyrosine protein kinase (DSTYK) mutations were detected in 2.2% of patients with congenital abnormalities of the kidney and urinary tract, suggesting that DSTYK is a major determinant of human urinary development, downstream of fibroblast growth factor (FGF) signaling. Methods and kits are provided for identifying and treating subjects at greater risk of developing CAKUT based on the presence of DSTYK mutations. Techniques include obtaining a biological sample from a subject and determining if the biological sample indicates a mutation of a gene for DSTYK. If it is determined that the biological sample indicates the mutation of the gene for DSTYK, then it is determined that the subject has or is at risk of developing CAKUT.

2 Claims, 16 Drawing Sheets

Specification includes a Sequence Listing.

(56) References Cited

OTHER PUBLICATIONS

ISA/US, "International Search Report and Written Opinion for the corresponding PCT application US2014/034056", dated Sep. 22, 2014, pp. 1-10.
Tashiro et al., "Nedo Human cDNA Sequencing Project: Unnamed Protein Product (*Homosapiens*)", Jan. 9, 2008, Publisher: GenBank, Published in: http://www.ncbi.nlm.nih.gov/sviewer/viewer.fcgi?noredirect=1&db=protein&val=BAF83774.1.
Abe, G., et al., "Function of FGF signaling in the developmental process of the median fin fold in zebrafish," Dev. Biol., 2007, pp. 355-366, vol. 304.
Bates, C.M., "Role of fibroblast growth factor receptor signaling in kidney development," American Journal of Physiology Renal Physiology, 2011, pp. F245-F251, vol. 301.
Corson, L.B., et al., "Spatial and temporal patterns of ERK signaling during mouse embryogenesis," Development, 2003, pp. 4527-4537, vol. 130.
Griffin, K.J., et al., "Interplay between FGF, one-eyed pinhead, and T-box transcription factors during zebrafish posterior development," Dev. Biol., 2003, pp. 456-466, vol. 264.
Gudbjartsson, D.F., et al., "Allegro, a new computer program for multipoint linkage analysis," Nat. Genet, 2000, pp. 12-13, vol. 25.
Poladia, D.P., et al., "Role of fibroblast growth factor receptors 1 and 2 in the metanephric mesenchyme," Developmental biology, 2006, pp. 325-339, vol. 291.
Sanna-Cherchi, S., et al., "Genetic approaches to human renal agenesis/hypoplasia and dysplasia," Pediatr. Nephrol, 2007, pp. 1675-1684, vol. 22.
Sanna-Cherchi, S., et al. "Renal outcome in patients with congenital anomalies of the kidney and urinary tract," Kidney Int., 2009, pp. 528-533, vol. 76.
Sanna-Cherchi, S, et al. "Copy-number disorders are a common cause of congenital kidney malformations," Am. J. Hum. Genet, 2012, pp. 987-997, vol. 91.
Schedl, A., "Renal abnormalities and their developmental origin," Nat. Rev. Genet, 2007; pp. 791-802, vol. 8.
Wang, K., et al., "Penn CNV: an integrated hidden Markov model designed for high-resolution copy number variation detection in whole-genome SNP genotyping data," Genome Res., 2007, pp. 1665-1674, vol. 17.
Weber, S., et al., "Prevalence of mutations in renal developmental genes in children with renal hypodysplasia: results of the ESCAPE study," J. Am. Soc. Nephrol, 2006, pp. 2864-2870, vol. 17.
Zhao, H., et al., "Role of fibroblast growth factor receptors 1 and 2 in the ureteric bud," Developmental biology, 2004, pp. 403-415, vol. 276.
Tashiro, H., et al., "NEDO Human cDNA Sequencing Project: Unnamed Protein Product (*Homosapiens*)", Jan. 9, 2008, Publisher: GenBank, Published in: http://www.ncbi.nlm.nih.gov/sviewer/viewer.fcgi?noredirect=1&db=protein&val=BAF83774.1.
Weng, P.L., et al., "A Recessive Gene for Primary Vesicoureteral Reflux Maps to Chromosome 12p11-q13," J Am Soc Nephrol 2009, pp. 1633-1640, vol. 20.
Xie, J., et al., "Predicting Progression of IgA Nephropathy: New Clinical Progression Risk Score," PLoS One 2012, pp. 1-9, vol. 7, No. 6, Publisher: Public Library of Science, Published in: http://www.plosone.org/article/fetchObject.action?uri=info%3Adoi%2F10.1371%2Fjournal.pone.0038904&representation=PDF.
Xie, J., et al., "Fine Mapping Implicates a Deletion of CFHR1 and CFHR3 in Protection from IgA Nephropathy in Han Chinese," J Am Soc Nephrol 2016, pp. 3187-3194, vol. 27.
Yu, X.Q., et al., "A genome-wide association study in Han Chinese identifies multiple susceptibility loci for IgA nephropathy," Nature Genetics 2012, pp. 178-182, vol. 44, No. 2, Publisher: Nature Publishing Group, Published in: http://www.nature.com/ng/journal/v44/n2/fulling.1047.html.
NCBI Reference Sequence: NM_015375.2 "*Homo sapiens* dual serine/threonine and tyrosine protein kinase (DSTYK), transcript variant 1, mRNA"; Aug. 5, 2014.

NCBI Reference Sequence: XP_001765144.1 "Qa-SNARE, Sso1/Syntaxin1-type, SYP12A-group [Physcomirella patens]"; Aug. 29, 2014.
GENBANK: BAC87313.1 "Unnamed Protein Product [*Homo sapiens*]"; Aug. 29, 2014.
GENBANK: FR833085.1 "Albugo laibachii Alem1, genomic contig CONTIG_87_Em1_cons_v4_86971_235_62031"; Aug. 29, 2014.
Zhou, X., et al, "HLA-DPB1 and DPB2 Are Genetic Loci for Systemic Sclerosis: A genome-wide association study in Koreans with replication in North Americans," Arthritis and Rheumatism 2009, pp. 3807-3814, vol. 60, No. 12, Publisher: John Wiley and Sons, Published in: http://onlinelibrary.wiley.com/doi/10.1002/art.24982/abstract.
Barrat, J., et al., "IgA Nephropathy," Journal of the American Society of Nephrology 2005, pp. 2088-2097, vol. 16, No. 7, Publisher: American Society of Nephrology, Published in: http://jasn.asnjournals.org/content/16/7/2088.full.
Beerman, I., et at al., "The genetics of IgA nephropathy," Nat Clin Pract Nephrol 2007, pp. 325-328, vol. 6, No. 3, Publisher: Nature Publishing Group, Published in: http://www.nature.com/nrneph/journal/v3/n6/full/ncpneph0492.html.
Bisceglia, L., et al., "Genetic Heterogeneity in Italian Families with IgA Nephropathy: Suggestive Linkage for Two Novel IgA Nephropathy Loci," American Journal of Human Genetics 2006, pp. 1130-1134, vol. 79, No. 6, Publisher: The American Society of Human Genetics, Published in: http://www.ncbi.nlm.nih.gov/pubmed/17186473.
Burton, P., et al., "Genome-wide association study of 14,000 cases of seven common diseases and 3,000 shared controls," Nature 2007, pp. 661-678, vol. 447, Publisher: Nature Publishing Group, Published in: http://www.nature.com/nature/journal/v447/n7145/abs/nature05911.html.
Craddock, N. et al., "Genome-wide association study of CNVs in 16,000 cases of eight common diseases and 3,000 shared controls," Nature 2010, pp. 713-720, vol. 464, Publisher: Nature Publishing Group.
Davila, S., et al., "Genome-wide association study identifies variants in the CFH region associated with host susceptibility to meningococcal disease," Nature Genetics 2010, pp. 772-776, vol. 42, No. 9, Publisher: Nature Publishing Group, Published in: http://www.nature.com/ng/journal/v42/n9/full/ng.640.html.
Debakker, P.I., et al., "A high-resolution HLA and SNP haplotype map for disease association studies in the extended human MHC," Nature Genetics 2006, pp. 1166-1172, vol. 38, No. 10, Publisher: Nature Publishing Group, Published in: http://www.nature.com/ng/journal/v38/n10/full/ng1885.html.
Ellington, A.D. and Szostak, J.W., "Selection in vitro of single-stranded DNA molecules that fold into specific ligand-binding structures," Nature 1992, pp. 850-852, vol. 355.
Feehally, J., et al., "HLA Has Strongest Association with IgA Nephropathy in Genome-Wide Analysis," Journal of the American Society of Nephrology 2010, pp. 1791-1797, vol. 21, No. 10, Publisher: The American Society of Nephrology, Published in: http://jasn.asnjournals.org/content/21/10/1791.full.pdf+html.
Feehally, J, et al., "Genome-Wide Analysis Identifies Strong Association Between HLA and IgA Nephropathy," J Am Soc Nephrol 2010, pp. 1-7.
Genetics Home Reference, "Genetic Conditions—Atypical hemolytic-uremic syndrome," http://ghr.nlm.gov/condition/atypical-hemolytic-uremic-syndrome, retrieved on Jul. 18, 2012, pp. 1-5.
Gharavi, A.G., et al., "IgA nephropathy, the most common cause of glomerulonephritis, is linked to 6q2223," Nature Genetics 2000, pp. 354-357, vol. 26, Publisher: Nature Publishing Group, Published in: http://www.nature.com/ng/journal/v26/n3/full/ng1100_354.html.
Gharavi, A.G., et al., "Aberrant IgA1 Glycosylation is Inherited in Familial and Sporadic IgA Nephropathy," Journal of the American Society of Nephrology 2008, pp. 1008-1014, vol. 19, No. 5, Publisher: The American Society of Nephrology, Published in: http://jasn.asnjournals.org/content/19/5/1008.full.pdf.
Gharavi, A.G., et al., "Genome-wide association study identifies susceptibility loci for IgA nephropathy", "Nature Genetics", 2011, pp. 321-327, vol. 43, Publisher: Nature Publishing Group, Published in: http://www.nature.com/ng/journal/v43/n4/full/ng.787.html.

(56) References Cited

OTHER PUBLICATIONS

Gusev, A., et al., "Whole population, genome-wide mapping of hidden relatedness," Genome Research 2009, pp. 318-326, vol. 19, Publisher: Cold Spring Harbor Laboratory Press, Published in: http://genome.cshlp.org/content/19/2/318.long.

Hastings, M.C., et al., "Galactose-Deficient IgA1 in African Americans with IgA Nephropathy: Serum Levels and Heritability," Journal of the American Society of Nephrology 2010, pp. 2069-2074, vol. 5, No. 11, Publisher: American Society of Nephrology, Published in: http://cjasn.asnjournals.org/content/5/11/2069.full.pdf.

Hermann, T. and Patel, D.J., "Adaptive recognition by nucleic acid aptamers," Science 2000, pp. 820-825, vol. 287.

Hsu, S., "Evidence for genetic factors in the development and progression of IgA nephropathy," Kidney International 2000, pp. 1818-1835, vol. 57, No. 5, Publisher: Nature Publishing Group, Published in: http://www.nature.com/ki/journal/v57/n5/pdf/4491515a.pdf.

Hughes, A.E., et al., "A common CFH haplotype, with deletion of CFHR1 and CFHR3, is associated with lower risk of age-related macular degeneration," Nature Genetics 2006, pp. 1173-1173, vol. 38, No. 10, Publisher: Nature Publishing Group, Published in: http://www.nature.com/ng/journal/v38/n10/full/ng1890.html.

IGA Nephropathy Support Network, "About the IgA Nephropathy Support Group," retrieved on Jul. 18, 2012, pp. 1-3.

ISA/US: International Search Report and Written Opinion, International Patent Application No. PCT/US12/025742, dated Sep. 24, 2012, pp. 1-6.

ISA/US: International Search Report and Written Opinion, International Patent Application No. PCT/US14/34056, dated Sep. 22, 2014, pp. 1-10.

Kamatani, Y., et al., "A genome-wide association study identifies variants in the HLA-DP locus associated with chronic hepatitis B in Asians," Nature Genetics 2009, pp. 591-595, vol. 41, No. 5, Publisher: Nature Publishing Group, Published in: http://www.nature.com/ng/journal/v41/n5/pdf/ng.348.pdf.

Kim, Y., et al., "Uteroglobin gene polymorphisms affect the progression of immunoglobulin A nephropathy by modulating the level of uteroglobulin expression," Pharmacogenetics 2001, pp. 299-305, vol. 11, No. 4, Publisher: Nature Publishing Group, Published in: http://www.ncbi.nlm.nih.gov/pubmed/11434507.

Kiryluk, K., et al., "Discovery of new risk loci for IgA nephropathy implicates genes involved in immunity against intestinal pathogens," Nature Genetics 2014, pp. 1187-1196, vol. 46, No. 11.

Kiryluk, K. and Novak, J., "The genetics and immunobiology of IgA nephropathy," J Clin Invest. 2014, pp. 2325-2332, vol. 124, No. 6.

Kiryluk, K., "Genetic Susceptibility, HIV Infection, and the Kidney," Journal of the American Society of Nephrology 2007, pp. S25-S35, vol. 2, Publisher: American Society of Nephrology, Published in: http://cjasn.asnjournals.org/content/2/Supplement_1/S25.full.pdf.

Kiryluk, K., et al., "Genetic studies of IgA nephropathy: past, present, and future," Pediatric Nephrology 2010, pp. 2257-2268, vol. 25, No. 11, Publisher: International Pediatric Nephrology Association, Published in: http://link.springer.com/article/10.1007%2Fs00467-010-1500-7.

Kiryluk, K., et al., "IgA nephropathy the case for a genetic basis becomes stronger," Nephrology Dialysis Transplantation 2010, pp. 336-338, vol. 25, No. 2, Publisher: Oxford Journals, Published in: http://ndt.oxfordjournals.org/content/25/2/336.full.pdf.

Kiryluk, K., et al., "Aberrant glycosylation of IgA1 is inherited in both pediatric IgA nephropathy and HenochSchoenlein purpura nephritis," Kidney International 2011, pp. 79-87, vol. 80, No. 1, Publisher: Nature Publishing Group, Published in: http://www.nature.com/ki/journal/v80/n1/full/ki201116a.html.

Kiryluk, K., et al, "Geographic Differences in Genetic Susceptibility to IgA Nephropathy: GWAS Replication Study and Geospatial Risk Analysis," PLOS Genetics 2012, pp. 1-16, vol. 8, No. 6, Publisher: Public Library of Science, Published in: http://www.plosgenetics.org/article/fetchObject.action?uri=info%3Adoi%2F10.1371%2Fjournal.pgen.1002765&representation=PDF.

Kiryluk, K., et al., "Pathogenesis of immunoglobulin A nephropathy: recent insight from genetic studies," Annual Review of Medicine 2013, pp. 339-356, vol. 64, Publisher: Annual Reviews, Published in: http://www.annualreviews.org/doi/abs/10.1146/annurev-med-041811-142014?url_ver=Z39.88-2003&rfr_dat=cr_pub%3Dpubmed&rfr_id=ori%3Arid%3Acrossref.org&jou.

Li, X., et al., "Advances in molecular genetics research of IgA nephropathy," Journal of Central South University Medical Sciences 2011, pp. 1120-1124, vol. 36, No. 11, Publisher: Central South University, Published in: http://xbyx.xysm.net/xbwk/fileup/PDF/2011111120.pdf.

Li, G., et al., "Variants of C1GALT1 gene are associated with the genetic susceptibility to IgA nephropathy," Kidney International 2007, pp. 448-453, vol. 71.

Lin, X., et al., "Aberrant galactosylation of IgA1 is involved in the genetic susceptibility of Chinese patients with IgA nephropathy," Nephrology Dialysis Transplant 2009, pp. 3372-3375, vol. 24, No. 11, Publisher: Oxford Journals, Published in: http://ndt.oxfordjournals.org/content/24/11/3372.full.pdf.

Maillard, N., et al., "Current Understanding of the Role of Complement in IgA Nephropathy," J Am Soc Nephrol 2015, pp. 1503-1512, vol. 26.

Malik, T.H., et al., "A Hybrid CFHR3-1 Gene Causes Familial C3 Glomerulopathy," J Am Soc Nephrol 2012, pp. 1155-1160, vol. 23.

Moldoveanu, M., et al., "Patients with IgA nephropathy have increased serum galactose-deficient IgA1 levels," Kidney International 2007, pp. 1148-1154, vol. 71, No. 11, Publisher: Nature Publishing Group, Published in: http://www.nature.com/ki/journal/v71/n11/full/5002185a.html.

Moore, I., et al., "Association of factor H autoantibodies with deletions of CFHR1, CFHR3, CFHR4, and with mutations in CFH, CFI, CD46, and C3 in patients with atypical hemolytic uremic syndrome," Blood 2010, pp. 379-387, vol. 115, No. 2, Publisher: American Society of Hematology, Published in: http://bloodjournal.hematologylibrary.org/content/115/2/379.full.pdf.

Papeta, N.,et al., "APOL1 variants increase risk for FSGS and HIVAN but not IgA nephropathy," Journal of American Society of Nephrology 2011, pp. 1991-1996, vol. 22, No. 11, Publisher: American Society of Nephrology, Published in: http://jasn.asnjournals.org/content/22/11/1991.full.pdf.

Paterson, A., et al., "Genome-Wide Linkage Scan of a Large Family with IgA Nephropathy Localizes a Novel Susceptibility Locus to Chromosome 2q3," Journal of the American Society of Nephrology 2007, pp. 2408-2415, vol. 18, No. 8, Publisher: American Society of Nephrology, Published in: http://jasn.asnjournals.org/content/18/8/2408.full.pdf.

Peng, J., et al., "Dusty protein kinases: primary structure, gene evolution, tissue specific expression and unique features of the catalytic domain," Biochimica et Biophysica Acta 2006, pp. 562-572, vol. 1759, Nos. 11-12.

Raychaudhuri, S., et al., "Associations of CFHR1-CFHR3 deletion and a CFH SNP to age-related macular degeneration are not independent," Nature Genetics 2010, pp. 553-555, vol. 42, No. 7, Publisher: Nature Publishing Group, Published in: http://www.nature.com/ng/journal/v42/n7/full/ng0710-553.html.

Renkema, K.Y., et al., "Novel perspectives for investigating congenital anomalies of the kidney and urinary tract (CAKUT)," Nephrol Dial Transplant. 2011, pp. 3843-3851, vol. 26, No. 12.

Remen et al., "Gene Gain and Loss During Evolution of Obligate Parasitism in the White Rust Pathogen of *Arabidopsis*: Albugo Laibachii Alem 1, Genomic Contig", Apr. 12, 2011, Publisher: GenBank, Published in: http://www.ncbi.nlm.nih.gov/pubmed/21750662.

Rensing, S.A. et al., "The Physcomitrella Genome Reveals Evolutionary Insights Into the Conquest of Land by Plants", May 22, 2009, pp. 64-69, vol. 319, No. 5859, Publisher: NCBI, Published in: http://www.ncbi.nlm.nih.gov/pubmed/18079367.

Sanna-Cherchi, S., et al., "Localization of a Gene for Nonsyndromic Renal Hypodysplasia to Chromosome 1p32-33," The American Journal of Human Genetics 2007, pp. 539-549, vol. 80, Issue 3.

(56) References Cited

OTHER PUBLICATIONS

Singer, J.B., et al., "A genome-wide study identifies HLA alleles associated with lumiracoxib-related liver injury," Vature Genetics 2010, pp. 711-714, vol. 42, No. 8, Publisher: Nature Publishing Group, Published in: http://www.nature.com/ng/journal/v42/n8/full/ng.632.html.

Song, R., et al., "Genetics of Congenital Anomalies of the Kidney and Urinary Tract", 2011, pp. 353-364, vol. 26, Publisher: Pediatr Nephrol, Published in: http://www.ncbi.nlm.nih.gov/pubmed/20798957.

Suzuki, H., et al., "The Pathophysiology of IgA Nephropathy," Journal of the American Society of Nephrology 2011, pp. 1795-1803, vol. 22, No. 10, Publisher: American Society of Nephrology, Published in: http://jasn.asnjournals.org/content/22/10/1795.long.

Kemen et al., "Gene Gain and Loss During Evolution of Obligate Parasitism in the White Rust Pathogen of *Arabidopsis*: Albugo laibachii Alem1, Genomic contig CONTIG_87_Em1_cons_v4_86971_235_62031", GenBank: FR833085.1: GenBank: FR833085, The Sainsbury Laboratory, John Innes Centre, Norwich, United Kingdom, Apr. 12, 2011, pp. 1-6.

Kemen et al., "Gene Gain and Loss During Evolution of Obligate Parasitism in the White Rust Pathogen of *Arabidopsis thaliana*", PLoS Biol., Jul. 5, 2011, pp. 1-41.

Rensing et al., "The Physcomitrella Genome Reveals Evolutionary Insights Into the Conquest of Land by Plants", Science, Dec. 13, 2007, pp. 64-69, vol. 319.

Rensing et al., "The Physcomitrella Genome Reveals Evolutionary Insights Into the Conquest of Land by Plants: Qa-SNARE, Sso1/Syntaxin1-Type, SYP12A-Group", NCBI Reference Sequence: XP001765144.1, Science, May 22, 2009, pp. 1-2.

Tashiro et al., "NEDO Human cDNA Sequencing Project: Unnamed Protein Product (*Homosapiens*)", GenBank: BAC87313.1, Jan. 9, 2008, pp. 1-2.

\* cited by examiner

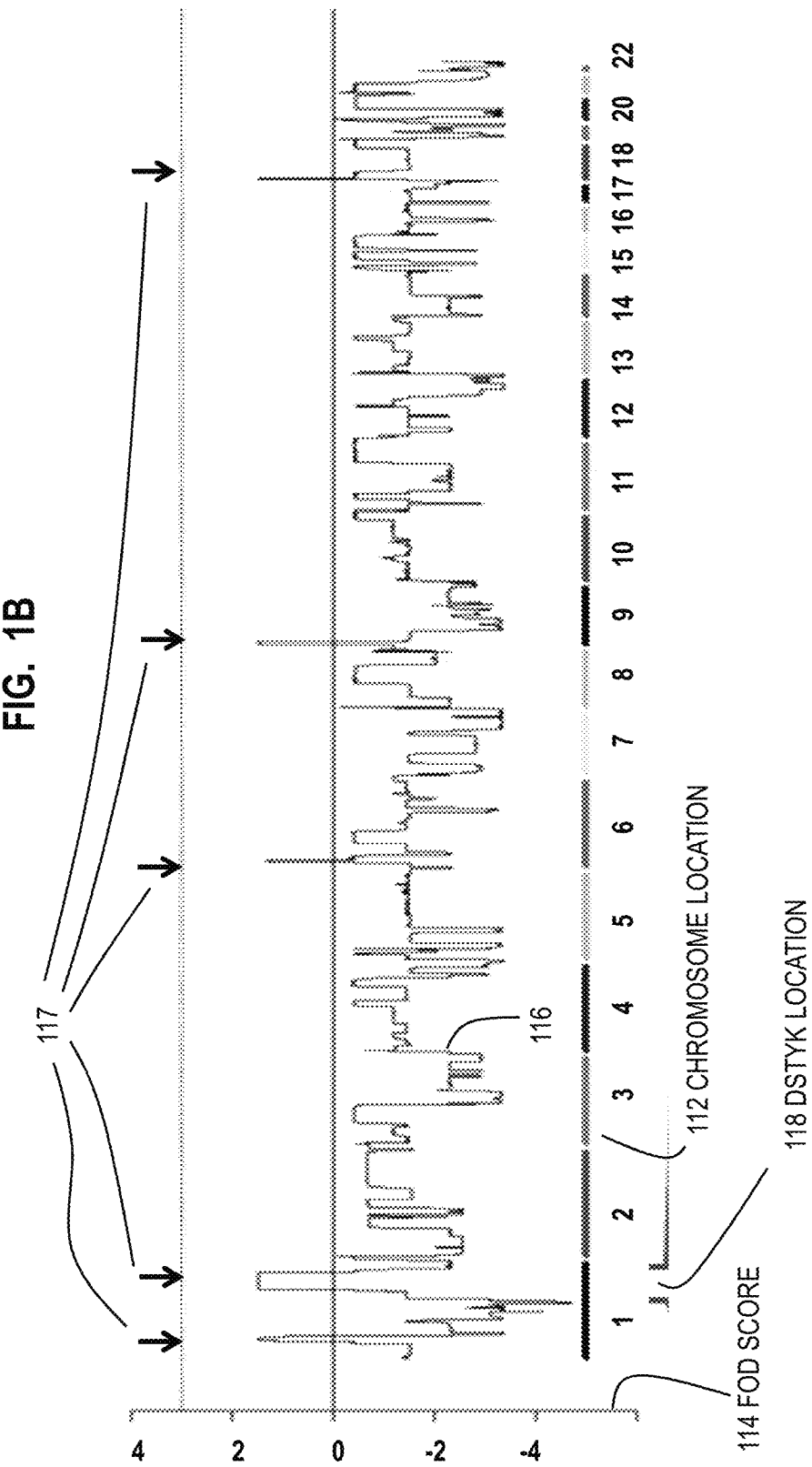

FIG. 3

| Variant | Consequence | Polyphen2 Prediction Score | Ethnicity | Sex | Age at Diagnosis | Phenotype | Familial/Sporadic disease | Chronic Renal Failure/ Dialysis | Extraurinary Tract Defects |
|---|---|---|---|---|---|---|---|---|---|
| Splice site/Truncating Mutations | | | | | | | | | |
| c.654+1 G>A | Val212_Gln218del | NA | Italian | M & F | 1.37 yrs | RHD, UPJO & | Familial (K100) | Yes (10) 7, 8 & 13 | Epilepsy (10) 7, 8, & 13 |
| c.24G>A | p.W8X | NA | Macedonian | M | 2 yrs | UPJO | Sporadic | No | Hemiparesis/ Ataxia (resolved) Hearing loss |
| c.655-3 C>T | | NA | Italian | F | At birth | UPJO | Familial | No | Hypercalciuria |
| Missense Mutations | | | | | | | | | |
| c.866>A | p.R230 | Prob D (0.997) | Albanian Italian Albanian | M M F | 5 yrs Prenatal At birth | UPJO RHD RHD | Sporadic Sporadic Sporadic | No Yes No | Congenital adrenal hyperplasia |
| c.599A>G | p.D200G | Prob D (0.997) | Italian | M | At birth | UPJO | Sporadic | No | Hearing loss |
| c.2528 C>T | p.S843L | Poss D (0.748) | Croatian | M | 9 months | CHN | Sporadic | Yes | Factor VII deficiency Hypercalciuria |

SEQUENCE LISTING

<160> NUMBER OF SEQ ID NOS: 101

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 1
agcggaactg gaggaagtgg acgttgtg                                28

<210> SEQ ID NO 2
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 2
gccatgaggc agc                                                13

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 3
cccttctagg aag                                                13

<210> SEQ ID NO 4
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 4
tgtgccaggg ctt                                                13

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 5
atgagggtgc tgc                                                13

<210> SEQ ID NO 6
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 6
tctgcttagg ctc                                                13

<210> SEQ ID NO 7
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 7

Val Thr Met His His Ala Leu Leu Gln
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 8

Met Glu Gly Asp Gly Val Pro Xaa
1               5

<210> SEQ ID NO 9

<400> SEQUENCE: 9

000

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Gly Gly Met Ile Arg Glu Leu Cys Arg Gly Phe Gly Arg Tyr Arg Arg
1               5                   10                  15

Tyr

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Glu Val Gln Glu Asn Asn Glu Asp Ala Ala His Val Leu Ala Glu Leu
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Gly Ile Leu Phe Trp Tyr Ile Cys Ser Gly Ser Val Lys Leu Pro Glu
1               5                   10                  15

Ala

<210> SEQ ID NO 13
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 13
gtcattagcg cattaaatgg t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
tactgatgaa gaaacaaggt g                                              21

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
cacatcatgt agattttgag ag                                             22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
cataagtacg tatataccca c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
atgaaatttc catctccgca g                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
aagatggaac atgtgggcac                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
atcatgtagt ggagacactg                                                20
```

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20 tgggtctttta agtaccactc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
aagggatatg tcttgaagtg                                               20

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
actagaagca ggtgtcctg                                                19

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
catgacaaca gattctagtg                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
agccttagga aagctctcac                                               20

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
gtgaattcag aaaaggctca g                                             21

<210> SEQ ID NO 26
<211> LENGTH: 21
<212> TYPE: DNA
<213> ORGANISM: Artificial Sequence
<220> FEATURE:

<223> OTHER INFORMATION: Synthetic oligonucleotide

<400> SEQUENCE: 26
tttagtcctt gccaaaagct g                                          21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
aaacaaggct aatcttggca c                                          21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cactgctgtt tacgtagcag                                            20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
gtaattatcc tcttgcacct c                                          21

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ggggtctgaa taagcatgac                                            20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gcctgcttcc tcttaatgag                                            20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ccaacaaacc tctgtctcac                                            20

```
<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
actgccacct actgattgac                                                     20

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
gtgtgacaca aaagtgtaca g                                                   21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
agccgaagaa atatgttggt c                                                   21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
tccaaaatga acaagcacga g                                                   21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
tcgtgcttgt tcattttgga g                                                   21

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 38
tcctgaagga aaagagctg                                                      19

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 39
tagtggggca ttcgaatcag                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
cagtgcttag agtactgcac                                              20

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
tattcttagg ggaggattga g                                            21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
ggaaattgct aagttctgga g                                            21

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
taacaggtgt ctggaggctg                                              20

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
ggcttggcga gtgtggtc                                                18

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ggatgaggtg taccgtacag                                              20

<210> SEQ ID NO 46
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 46
agtgctcaca aggccttgtc                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
ctgctgagtg aaggctacag                                               20

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
gaagctctga tttagccaca c                                             21

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
ccaagactgc tgtgattgtg                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
agatccgtgg caagaaccag                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
ccgagtcatt gttccaggac                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
```
tttgaggcag gccttgtgag                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
catcgtgttg gaaactgctc                                          20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
agtttgaagg agacctacag                                          20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
atctcctgtg taacaggctc                                          20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
acttccgaga aagttcagac                                          20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
tctacctgag gagatgggag                                          20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
gcttgccaca acctctgcac                                          20

<210> SEQ ID NO 59
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 59
ctgcaggaag tgtgcctcag                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
taagcaggga cctctcgcag                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
cctcaagtcc tgaagttgag                                               20

<210> SEQ ID NO 62
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 62
ggcaggtgat agggatcag                                                19

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ccacctttct tctcaagctc                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
ttcagccacc atctgaacac                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
aagtcagctc agccacactg                                               20
```

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tggacaaaga gcagagactg                                                        20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
aatcgctgag gaacttggga                                                        20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
ttcctgcctt tctctaggtg                                                        20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ccttatgtcc tctgcttctc                                                        20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
gtccaaggac aaagcatgtg                                                        20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
ctgtgaggga attgcagctc                                                        20

<210> SEQ ID NO 72
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 72
tgagggccag agggaacat                                                    19

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
tcctcagcca gatctctgag                                                   20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
caatgctggc tatgcatgtg                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cggtttcacc aagtcaggtc                                                   20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
tagaagcctc gttctctctg                                                   20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
gtaccctggt gtgagtagag                                                   20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
cagaccattc agcagctcac                                                   20

<210> SEQ ID NO 79

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 79
ctgcaaacca ctgctattct g                                          21

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
ctggaaatgg ttcttggctc                                            20

<210> SEQ ID NO 81
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 81
atgcctccta gaaccggag                                             19

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
gtgctgcact aacaagcctg                                            20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
ttgttctcct gtttgtcctc                                            20

<210> SEQ ID NO 84
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 84
ggtgatgtga agggttgcg                                             19

<210> SEQ ID NO 85
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 85
```
ttacagrtac ca                                                          12

<210> SEQ ID NO 86
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 86
tggtacctgt aa                                                          12

<210> SEQ ID NO 87
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 87
tctcttacag krmstr                                                      16

<210> SEQ ID NO 88
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 88
tctcttacag gaagtg                                                      16

<210> SEQ ID NO 89
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 89
kswaytrsag gaagtg                                                      16

<210> SEQ ID NO 90
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 90
cacttcctcc agttcc                                                      16

<210> SEQ ID NO 91
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 91
tctcttacag gaagtg                                                      16

<210> SEQ ID NO 92
<211> LENGTH: 16
<212> TYPE: DNA

```
<213> ORGANISM: Artificial Sequence
<220> FEATURE:
<223> OTHER INFORMATION: Synthetic oligonucleotide

<400> SEQUENCE: 92
cacttcctgt aagaga                                                        16

<210> SEQ ID NO 93
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 93
agcggaactg gaggtaacga tgcaccatgc tctcttacag gaagtggacg ttgtg            55

<210> SEQ ID NO 94
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 94
atcagggcaa ctgggagac                                                    19

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
tgttccacca acatgctctg                                                   20

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 96
acactggccg tgtaccttca gtccc                                              25

<210> SEQ ID NO 97
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 97
acatttatac tccattcaca tgat                                               24

<210> SEQ ID NO 98
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 98
cuacuaacau ggaguuuaa                                                     19
```

```
<210> SEQ ID NO 99
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 99
ggagacacgu uugcagaua                                                    19

<210> SEQ ID NO 100
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 100
gaauuucacu auaugaggu                                                    19

<210> SEQ ID NO 101
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 101
ccacaaagau gaacucucu                                                    19
```

MUTATIONS IN DSTYK CAUSE DOMINANT URINARY TRACT MALFORMATIONS

CROSS-REFERENCE TO RELATED APPLICATIONS

This application is a 371 national stage application of PCT Application No. PCT/US2014/034056, filed Apr. 14, 2014, and claims the benefit of U.S. Provisional Application No. 61/811,365, filed on Apr. 12, 2013; the entire contents of which are hereby incorporated by reference as if fully set forth herein.

STATEMENT OF GOVERNMENT INTEREST

This invention was made with Government support under grant DK080099 awarded by the National Institutes of Health. The Government has certain rights in the invention.

BACKGROUND

Congenital abnormalities of the kidney and the urinary tract (CAKUT) are the most common cause of pediatric kidney failure. These disorders are highly heterogenous, and their etiology is poorly understood. Many forms of CAKUT are familial, but because they may be asymptomatic, they require large-scale clinical screening in order to be identified. CAKUT contributes to 23% of birth defects,[1,2] accounting for 40-50% of pediatric and 7% of adult end-stage renal disease (ESRD) worldwide.[3,4] These disorders are genetically heterogeneous and encompass a wide range of anatomic defects, such as renal agenesis (RA), renal hypoplasia (RHD)/dysplasia, uretero-pelvic junction obstruction (UPJO), or vesicoureteral reflux (VUR).[5] Mutations in genes that produce syndromic disorders, such as HNF1B and PAX2, are detected in only 5-10% of cases.[6,7] Familial forms of nonsyndromic disease have been reported, further supporting genetic determination;[8,9] but, owing to locus heterogeneity and small pedigree size, the genetic etiology for most familial or sporadic cases remains unknown.

SUMMARY

Techniques are provided for identifying subjects having CAKUT or at risk of developing CAKUT that directly target the pathogenesis of the disease. Applicants have identified six mutations in the gene for dual serine/threonine and tyrosine protein kinase (DSTYK) that are detected in 2.2% of patients with CAKUT. This suggests that DSTYK is a major determinant of human urinary tract development and functional studies indicated that DSTYK mediates fibroblast growth factor (FGF) signaling. By analyzing the DSTYK gene, it is possible to provide patients with (i) diagnosis of this form of CAKUT; (ii) screening in high risk families and populations for CAKUT; (iii) a definitive diagnosis for patients already affected, allowing for more accurate prognoses and earlier therapies; (iv) informed genetic counseling for patients and parents and (v) animal models with this form of CAKUT to develop novel methods of treatment.

In a first set of embodiments, a method includes obtaining a biological sample from a subject and determining if the biological sample indicates a mutation of a gene for dual serine/threonine and tyrosine protein kinase (DSTYK). If it is determined that the biological sample indicates the mutation of the gene for DSTYK, then it is determined that the subject has or is at risk of developing congenital abnormalities of the kidney and urinary tract (CAKUT).

In some embodiments of the first set, the method includes monitoring an unaffected kidney or unaffected urinary tract or both on a regular basis, if is determined that the biological sample indicates the mutation of the gene for DSTYK.

In a second set of embodiments, a kit includes a primer or probe that is complementary to and specifically hybridizes to or binds to a target comprising a DSTYK mutation in a nucleic acid sample.

In a third set of embodiments, a probe is provided that binds to a target comprising a protein encoded by a DSTYK mutation in a biological sample.

In a fourth set of embodiments, a method for treating cancer comprises introducing siRNA that interferes with expressing a gene for DSTYK.

These and other features, embodiments, and advantages of the present invention will become better understood with regard to the following description, appended claims, and accompanying drawings.

BRIEF DESCRIPTION OF THE DRAWINGS

The following figures form part of the present specification and are included to further demonstrate certain embodiments of the present invention. The invention may be better understood by reference to one or more of these drawings in combination with the detailed description of specific embodiments presented herein, in which:

FIG. 1B is a diagram that illustrates example linkage analysis that identifies five regions of the genome, according to an embodiment;

FIG. 3 is a table that illustrates example DSTYK mutations, corresponding protein mutations, and associated CAKUT symptoms, according to an embodiment.

DETAILED DESCRIPTION

Figure 1A:
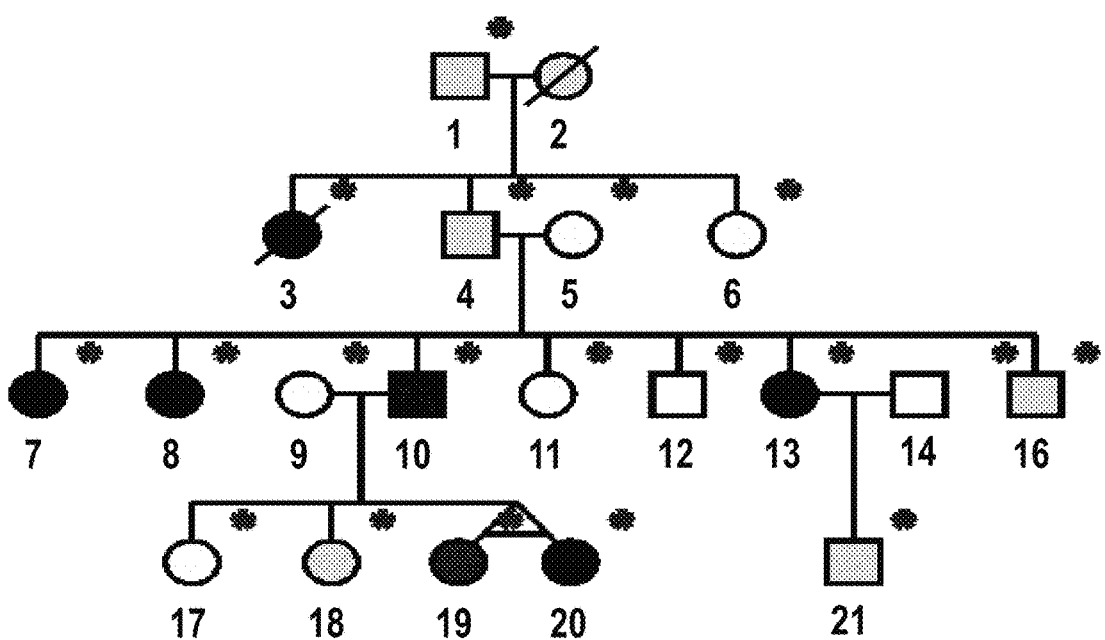
FIG. 1A is a diagram that illustrates example DSTYK mutations in a family with CAKUT, according to an embodiment.

In the following description, for the purposes of explanation, numerous specific details are set forth in order to provide a thorough understanding of the present invention. It will be apparent, however, to one skilled in the art that the present invention may be practiced without these specific details.

The reference sequence of DSTYK was downloaded from the National Center for Biotechnology Information (NCBI) database (Build 37.1); NCBI Gene ID 25778; genomic coordinates from Genome Reference Consortium release 37 (GRCh37) p10 Chromosome 1; NC_000001.10 with 249250621 base pairs (bp). The DSTYK gene comprises 69097 bp at positions from 205111631 to 205180727; corresponding to GenBank No. mRNA NM_015375.2 with 7926 bp as variant 1 and mRNA NM_199462.2 with 7791 bp as variant 2.

It has been discovered that DSTYK co-localizes with fibroblast growth factor (FGF) receptor type and type 2 (FGFR1 and FGFR2, respectively). In addition, small interfering RNA (siRNA), used to knockdown DSTYK in HEK293 cell lines, resulted in abrogation of extracellular-signal-regulated kinase (ERK) phosphorylation, which is a key signaling transduction event downstream of FGF signaling.

It was further discovered that mutations in DSTYK are associated with familial or sporadic disposition for and occurrence of congenital abnormalities of the kidney and the urinary tract (CAKUT). To explain these relationships and use of such relationships in diagnosis and treatment of CAKUT, the following definitions of terms and acronyms are provided.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing in various embodiments, example methods and materials are now described.

Generally, nomenclatures used in connection with, and techniques of, cell and tissue culture, molecular biology, immunology, microbiology, genetics, protein, and nucleic acid chemistry and hybridization described herein are those well-known and commonly used in the art.

TABLE 1

| | Definitions. |
|---|---|
| allele | A particular form of a genetic locus, distinguished from other forms by its particular nucleotide sequence, or one of the alternative polymorphisms found at a polymorphic site. |
| biological sample | A sample that may be extracted, untreated, treated, diluted, or concentrated from a subject. Any cell type or tissue may be used in various embodiments. DNA testing can be performed from any bodily fluid that includes genomic DNA, e.g., blood, tissue biopsies, hair follicles or skin. For prenatal subjects, fetal nucleic acid samples can be obtained from maternal blood, amniocytes or chorionic villi. Suitably, the biological sample is selected from any part of a subject's body, including, but not limited to hair, skin, nails, tissues or bodily fluids such as saliva, blood, plasma, and serum. |
| bp | Base pair; refers to one nucleotide on a strand of a nucleic acid that is paired with a corresponding nucleotide on the second strand of a double stranded DNA or RNA molecule. |
| CAKUT | Congenital anomalies of the kidney and urinary tract, including, but not limited to, ureteropelvic junction obstruction (UPJO), renal agenesis (RA), vesicoureteral reflux (VUR), renal hypodysplasia (RHD), and congenital hydronephrosis (CHN). |
| complementary nucleotide sequence | A sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the two molecules is preferably exact, i.e., 100%. If less selectivity is required, then routine experimentation can determine the level of complementarity that provides the desired result. |
| detecting a mutation | Applying any method useful for analyzing the DNA or amino acid sequence of a subject for the presence or absence of a mutation. Such methods for analyzing a DNA or amino acid sequence are well known to those of skill in the art and any suitable means of detecting a mutation are encompassed by the present embodiments. Such analysis may be done, for example, by isolating a genomic DNA sample from the subject and using nucleic acid hybridization with a detectable probe to test for the presence and/or absence of a mutation. Alternately, such analysis may be done using an mRNA sample from the subject, and optionally producing cDNA from the sample. Such analysis may also be done, for example, using polymerase chain reaction to amplify a nucleic acid sequence and the amplification product may be sequenced and/or used for hybridization with a probe to detect the mutation. Such analysis may also be done, for example, by isolating a protein sample from the subject and using |

TABLE 1-continued

| | Definitions. |
|---|---|
| | antibodies to test for the presence and/or absence of a mutation in the protein. |
| DNA | Deoxyribonucleic acid, a typically double stranded molecule, each strand comprising repeating chemical units known as "nucleotides" or "bases." There are four bases in DNA: adenine, thymine, cytosine, and guanine, represented by the letters A, T, C and G, respectively. |
| DSTYK | Dual serine/threonine and tyrosine protein kinase, a protein that serves as an enzyme. Multiple alternatively spliced transcript variants have been found, but the biological validity of some variants has not been determined. |
| DSTYK gene | A DNA sequence that codes for DSTYK. In the human genome, this gene comprises 69097 base pairs located at positions (locus) from 205111631 to 205180727 of the 249250621 base pairs of NC_000001.10 for Chromosome 1. |
| DSTYK mRNA | mRNA that codes for DSTYK. Two variants are previously known given by GenBank No. mRNA NM_015375.2 with 7926 by as variant 1 and mRNA NM_199462.2 with 7791 bp as variant 2. |
| DSTYK mutation | A DNA sequence at the position of the DSTYK gene that deviates from the reference sequence, especially a deviation that encodes for a change in at least one amino acid from the reference DSTYK. |
| gene | One or more sequence(s) of nucleotides in a genome that together encode one or more expressed molecules, e.g., an RNA, or polypeptide. The gene can include coding sequences that are transcribed into RNA which may then be translated into a polypeptide sequence, and can include associated structural or regulatory sequences that aid in replication or expression of the gene. A gene can include one or more sequences called exons that code for an expressed molecule and one or more sequences called introns that do not. |
| genetic predisposition/at risk of developing a disease | The susceptibility of a subject to a disease, such as CAKUT, by virtue of the subject having a certain variant of a gene, e.g., one or more DSTYK mutations. A subject who is "at risk of developing a disease" means that the subject has a statistically higher likelihood or susceptibility to the disease condition than control. Detecting a genetic predisposition includes detecting the risk of developing the disease, and determining the susceptibility of that subject to developing the disease or to having a poor prognosis for the disease. A subject who has a genetic predisposition to a disease will not necessarily develop the disease, but is at a higher than normal risk for developing the disease. |
| hybridize | To cause two complementary nucleic acid strands to anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, 2nd ed., Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, 2nd ed., Cold Spring Harbor Press, Plainview, N.Y.; Ausubel, F. M. et al. 1994, Current Protocols in Molecular Biology, John Wiley & Sons, Secaucus, N.J. |
| hybridizing specifically | Hybridizing with no significant cross-hybridization with DNAs or RNAs encoding other proteins under usual hybridization conditions, preferably under stringent hybridization conditions. Does not require sequences completely complementary to the target sequence but generally involves sequences at least 70%, preferably at least 80%, and more preferably at least 90% (e.g., 95% or more) identical to the target at the base sequence level. |
| kit | Any manufacture (e.g. a package or container) comprising at least one reagent (e.g., a medicament for treatment of a disease) or a probe for specifically detecting a biomarker gene or protein of various embodiments. In certain embodiments, the manufacture is promoted, distributed, or |

TABLE 1-continued

Definitions.

| | |
|---|---|
| | sold as a unit for performing one or more methods disclosed herein. |
| LD/linkage disequilibrium | Co-occurrence of two genetic loci (e.g., markers) at a frequency greater than expected for independent loci based on the allele frequencies. Linkage disequilibrium (LD) typically occurs when two loci are located close together on the same chromosome. When alleles of two genetic loci (such as a marker locus and a causal locus) are in strong LD, the allele observed at one locus (such as a marker locus) is predictive of the allele found at the other locus (for example, a causal locus contributing to a phenotypic trait). |
| linkage | The association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set. |
| locus | A location on a chromosome or DNA molecule corresponding to a gene or a physical or phenotypic feature, where physical features include polymorphic sites. |
| mRNA | Messenger RNA, a molecule transcribed from a gene that includes complimentary bases of exons and not introns. |
| mutation | One or more changes to the sequence of a DNA nucleotide sequence or a protein amino acid sequence relative to a reference sequence, usually a wild-type sequence. A mutation in a DNA sequence may or may not result in a corresponding change to the amino acid sequence of an encoded protein. A mutation may be a point mutation, i.e. an exchange of a single nucleotide and/or amino acid for another. Point mutations that occur within the protein-coding region of a gene's DNA sequence may be classified as a silent mutation (coding for the same amino acid), a missense mutation (coding for a different amino acid), and a nonsense mutation (coding for a stop which can truncate the protein). A mutation may also be an insertion, i.e. an addition of one or more extra nucleotides and/or amino acids into the sequence. Insertions in the coding region of a gene may alter splicing of the mRNA (splice site mutation), or cause a shift in the reading frame (frameshift), both of which can significantly alter the gene product. A mutation may also be a deletion, i.e. removal of one or more nucleotides and/or amino acids from the sequence. Deletions in the coding region of a gene may alter the splicing and/or reading frame of the gene. A mutation may be spontaneous, induced, naturally occurring, or genetically engineered. |
| NCBI | National Center for Biotechnology Information ( ) database (Build 37.1); NCBI Gene ID GRC. Genome Reference Consortium |
| oligonucleotide | A molecule comprising a chain of one or more nucleotides. Also called an oligio. |
| PCR | Polymerase chain reaction, a method to increase the quantity of a nucleic acid with a particular sequence by repeated hybridization and heating cycles. |
| peptide | A molecule made up of one or more amino acids. |
| polymorphism | A variation in a gene sequence. Polymorphisms can be referred to, for instance, by the nucleotide position at which the variation exists, by the change in amino acid sequence caused by the nucleotide variation, or by a change in some other characteristic of the nucleic acid molecule or protein that is linked to the variation. In the instant application "polymorphism" refers a traditional definition meaning that the minor allele frequency must be greater than at least 1%. |
| primer/probe | A function of an oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for |

TABLE 1-continued

Definitions.

| | |
|---|---|
| | amplification, detection or quantization of DSTYK may be used either as hybridization probes or as target binding sequences in primers for detection or amplification, optionally linked to a specialized sequence required by the selected amplification reaction or to facilitate detection. |
| protein | A long polypeptide made up of a chain of amino acids. 23 different amino acids are repeated in difference amino acid sequences to make up the proteins in the human body. |
| qPCR | Quantitative PCR, whereby relative levels of a sequence determined after amplification are the same as before amplification. |
| Reference DSTYK | The amino acid sequence for DSTYK encoded by the reference DSTYK gene given by NCBI Gene ID 25778. |
| Reference DSTYK gene | The nucleotide sequence for the DSTYK gene given by NCBI Gene ID 25778. |
| RNA | Ribonucleic acid, a double- or single-stranded molecule, each strand comprising a chain of nucleotides as in DNA, but in which uracil (U) replaces thymine (T). |
| single nucleotide polymorphism (SNP) | A DNA sequence among individuals in a population. SNP genotyping is the measurement of genetic variations of single nucleotide polymorphisms (SNPs) between members of a species. SNPs are one of the most common types of genetic variation. An SNP is a single base pair mutation at a specific locus, usually consisting of two alleles (where the rare allele frequency is >1%). SNPs are involved in the etiology of many human diseases. |
| siRNA | Small interfering RNA that often interferes with the expression of specific genes with complementary nucleotide sequences. |
| specific primer | An oligonucleotide or primer, under appropriate hybridization or washing conditions, capable of hybridizing to a target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned. |
| subject | A living multicellular organism for which diagnosis, treatment, or therapy is desired, particularly humans. In various embodiments, subjects include, but are not limited to, animals including mammals, which include hominoids (e.g., humans, chimpanzees, and monkeys) and laboratory test animals (e.g., rabbits, mice, rats, guinea pigs, hamsters) and plants. The term includes transgenic and cloned species. |
| therapeutically effective amount | An amount of a therapeutic agent that alone, or together with one or more additional therapeutic agents, induces a desired response, such as decreasing the risk of developing a disease or condition or decreasing the signs and symptoms or a disease or condition. |
| treatment | Steps taken to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder and/or its symptoms. |
| wild-type | Typical sequence or sequences of a gene and/or protein in nature, e.g., the most common sequence or sequences in the natural population. This may, however, over a period of time be replaced by another form and/or vary between populations within the same species. |

Overview

Foundational experiments indicated that: DSTYK localizes to cell membranes with high expression in maturing epithelia of all major organs; and, morpholino-induced knockdown of DSTYK in zebrafish resulted in multi-organ developmental defects resembling loss of Fibroblast Growth Factor (FGF) signaling. Further experiments revealed that DSTYK is expressed in the ureteric bud (UB) and metanephric mesenchyme (MM) during nephrogenesis, colocalizing with FGF receptors. DSTYK knockdown in human embryonic kidney cells inhibited FGF-stimulated ERK-phosphorylation.

Disruption of signals governing the reciprocal induction between the metanephric mesenchyme (MM) and the ureteric bud (UB)[18,19] results in developmental defects in the kidney or the lower urinary tract, or both structures[22,23]. The diversity of signaling pathways in nephrogenesis explains the significant locus heterogeneity of CAKUT, complicating the discovery of underlying genes[19]. For example, in a previous study of 522 patients with kidney malformations, 72 distinct copy number disorders were identified in 88 patients, suggesting that virtually every patient may have a unique genetic diagnosis[12].

In humans, there are twenty-two FGF ligands that signal through four FGF receptors, conferring both complexity and redundancy to this pathway[16,20]. Different combinations of FGF ligands are expressed in the UB, MM and renal stroma[16], and recently, a recessive FGF20 mutation was reported in a human family with renal agenesis[21]. FGFR1 and FGFR2 are responsible for most of the FGF signaling during nephrogenesis[16,22,23]. FGF receptor engagement results in autophosphorylation and activation the intracellular MAPK cascade, ultimately resulting in production of diphospho-ERK, the main effector of the FGF transcriptional program[16,20]. DSTYK is a positive regulator of ERK-phosphorylation downstream of FGF receptor activation. A prior study suggested a role for DSTYK in induction of apoptosis, a pathway also regulated by FGF signaling[24]. Additional studies are anticipated to delineate the precise role of DSTYK in this signal transduction cascade. Identification of other components of this pathway may elucidate additional forms of CAKUT in humans.

In the experiments described herein, independent mutations in DSTYK were identified as a novel cause of CAKUT in 2.2% of these patients. The identification of a heterozygous nonsense mutation suggests haploinsufficiency as a potential genetic mechanism, underscoring a critical role for DSTYK gene dosage in human urinary tract development. In yet another study, mutations were detected in patients with both ureteric and kidney parenchymal defects, consistent with DSTYK expression in the UB and MM. These data demonstrate the effectiveness of exome sequencing for elucidation of heterogeneous developmental traits with modest-sized pedigrees.

Some embodiments are based on these determinations that mutations in the DSTYK gene are associated with the presence or risk of developing CAKUT, and thus the mutations may be used as a marker for CAKUT. Exome sequencing was performed in a family with autosomal dominant nonsyndromic congenital urinary tract malformations. A segregating splice-site mutation was identified in DSTYK. Additional heterozygous mutations, including nonsense and splice-site mutations were detected in seven other unrelated patients. These mutations are summarized in the Table presented in FIG. 3.

As listed in FIG. 3, there are six mutations already identified in a population of subjects that exhibits or has a familial risk of developing CAKUT. The mutations are indicated by the changes in the cDNA complementary to the mRNA for DSTYK, indicated by the prefix "c.", the position relative to the start of the gene in the database, and the reference base at that location, an arrowhead pointing to the replacement base at that location. The cDNA sequences surrounding those mutations are listed in Table 2, with at least six bases on either side of the change to provide sequences with at least 13 bp.

TABLE 2 cDNA mutations and sequences.

| cDNA Mutation notation | Resulting sequence | Sequence ID |
|---|---|---|
| c.654 + 1G > A | AGCGGAACTGGAGGAAGT GGACGTTGTG | SEQ ID NO: 1 |
| c.24G > A | GCCATGAGGCAGC | SEQ ID NO: 2 |
| c.655 - 3 C > T | CCCTTCTAGGAAG | SEQ ID NO: 3 |
| c.86G > A | TGTGCCAGGGCTT | SEQ ID NO: 4 |
| c.599A > G | ATGAGGGTGCTGC | SEQ ID NO: 5 |
| c.2528C > T | TCTGCTTAGGCTC | SEQ ID NO: 6 |

The amino acid sequences of the resulting DSTYK variants are listed in Table 3. The amino acid single letter abbreviations, e.g., as used in Table 3, are given in Table 4.

TABLE 3

Protein mutations and sequences.

| cDNA Mutation notation | Protein mutation notation | Resulting sequence | Sequence ID |
|---|---|---|---|
| c.654 + 1G > A | Val210_Gln218del | VTMHHALLQ (deletion) | SEQ ID NO: 7 |
| c.24G > A | p.W8X | MEGDGVPX | SEQ ID NO: 8 |
| c.655 - 3 C > T | not applicable | not applicable (splice site mutation) | SEQ ID NO: 9 |
| c.86G > A | p.R29Q | GGMIRELCRGFGRYRRY | SEQ ID NO: 10 |
| c.599A > G | p.D200G | EVQENNEDAAHVLAEL | SEQ ID NO: 11 |
| c.2528C > T | p.S843L | GILFWYICSGSVKLPEA | SEQ ID NO: 12 |

TABLE 4

Amino acid abbreviations.

| letter | Amino acid |
|---|---|
| A | alanine |
| R | arginine |
| N | asparagine |
| D | aspartic acid |
| B | asparagine or aspartic acid |
| C | cysteine |
| E | glutamic acid |
| Q | glutamine |
| Z | glutamine or glutamic acid |
| G | glycine |
| H | histidine |
| I | isoleucine |
| L | leucine |
| K | lysine |
| M | methionine |
| F | phenylalanine |
| P | proline |
| S | serine |
| T | threonine |
| W | tryptophan |

TABLE 4-continued

Amino acid abbreviations.

| letter | Amino acid |
|---|---|
| Y | tyrosine |
| V | valine |

FIG. 3 is a table that illustrates example DSTYK mutations, corresponding protein mutations, and associated CAKUT, according to an embodiment. The protein and cDNA annotations are based on NP_056190.1 and NM_015375.2, respectively. All variants in this table were absent in dbSNP137, the exome variant server, and were not detected in 384 European controls. Note 1: Detailed phenotypes of all patients in K100 were determined. Note 2: This mutation was found in two siblings affected by obstructive uropathy. The c.655-3 C>T variant is predicted to decrease the consensus values (CV) for the canonical splice site from 96.68 to 89, corresponding to a −7.95% variation (Human Splicing Finder, HSF). Prob D=Probably damaging; Poss D=Possibly damaging; B=Benign. UPJO=ureteropelvic junction obstruction; RA=renal agenesis; VUR=vesicoureteral reflux; RHD=renal hypodysplasia; CHN=congenital hydronephrosis. N/A=not applicable.

In other embodiments, other mutations of the DSTYK gene are explored to determine whether a subject exhibits or is at risk of developing CAKUT. In such embodiments, mutations are detected in subjects who have a familial risk or exhibit CAKUT. If the nucleotide sequence deviates from the reference sequence, then a first incidence of the nucleotide sequence is determined in an affected population of affected members having CAKUT in the affected members or a family of the affected members. A second incidence of the nucleotide sequence is determined in a healthy population of healthy members not having CAKUT in the healthy members or a family of the healthy members. If the second incidence for the healthy population is about zero and the first incidence for the affected population is greater than about zero, then it is determined that a subject who exhibits the mutation has, or is at risk of developing, CAKUT.

Thus in various embodiments a method includes obtaining a biological sample from a subject. The biological sample in various embodiments includes hair, nails, serum, blood, sputum, plasma, saliva, mucosal scraping, amniotic fluid or tissue biopsy from a human being. It is then determined if the biological sample indicates a mutation of a gene for DSTYK, either in the genomic DNA, mRNA, or cDNA complimentary to the genomic DNA or mRNA, or in the amino acid sequences of the proteins produced. Nucleic acid mutations can be detected using one or more of such methods as oligonucleotide microarray analysis, allele-specific hybridization, allele-specific polymerase chain reaction (PCR), 5' nuclease digestion, molecular beacon assay, oligonucleotide ligation assay, size analysis, or nucleic acid sequencing. In some embodiments, a primer or probe is configured to indicate hybridization or binding by polymerase chain reaction (PCR), reverse transcription PCR (RT-PCR), fluorescence resonance energy transfer (FRET), chemiluminescence, enzymatic signal amplification, electron dense particles, magnetic particles, capacitance coupling or mass spectrometry. Protein mutations can be detected using one or more of such methods as immunostaining microscopy, immunoprecipitation, immunoelectrophoresis, western blot, bicinchoninic acid (BCA) assay, enzyme assay, and spectrophotometry.

If it is determined that the biological sample indicates the mutation of the gene for DSTYK, then it is determined that the subject has or is at risk of developing CAKUT.

In some embodiments, treatment varies based on determining that a subject has or is at risk of developing CAKUT. Once the mutation in the DSTYK gene is detected, the kidneys or urinary tract, or both, of the subject who has or is at risk of having CAKUT can be closely monitored (e.g., on a regular basis that is not appropriate for a member of an unaffected population) for early detection of a malformation or abnormality. As a consequence, surgical correction can be initiated when a malformation or abnormality is detected, and thus be performed more expeditiously, e.g., even before the subject becomes symptomatic. Thus, this screening method can be used to examine patients with CAKUT and determine if CAKUT is due to DSTYK mutations. This would change the management because the patients would be at risk for obstructive uropathy, which is a surgically correctable.

Kits comprising a primer or probe that is complementary to and specifically hybridizes to or binds to a target comprising a DSTYK mutation in a nucleic acid sample and enzymes suitable for amplifying nucleic acid are provided in certain embodiments. The primer or probe may be labeled with a radioisotope, a fluorophore, a chromophore, a dye, an enzyme, or time of flight (TOF) carrier. Other diagnostic kits are available for identifying a subject at risk of developing CAKUT comprising in one or more containers one or more probes capable of binding to a mutation in one or more regions of the DSTYK gene. In some embodiments, the mutation is one or more of those listed above in Table 3.

In these kits, binding may be detected by in situ hybridization, PCR RT-PCR, fluorescence resonance energy transfer, chemiluminescence enzymatic signal amplification, electron dense particles magnetic particles and capacitance coupling. In some embodiments, the probe is selected to allow the DNA to be sequenced to identify changes as compared to the wild-type sequence. One or more reagents that differentiate a normal DSTYK gene or protein from a mutant DSTYK gene or protein containing one or more mutation are present in the kit. These reagents in certain embodiments may comprise one or more nucleic acid probe one or more antibodies, may be in the form of a microarray, are suitable for primer extension and can comprise controls indicative of a healthy individual.

In various embodiments, detected mutations are used either diagnostically or prognostically, or both, for CAKUT. These results have particularly strong therapeutic implications for monitoring and treating diseases or disorders associated with impaired kidney function.

The methods of some embodiments can be used alone or in combination with other diagnostic tools to confirm a diagnosis, e.g., diagnostic tools based on behavior. Various embodiments also facilitate the development of personalized therapies based on the underlying genetic cause of CAKUT. Patients who respond well to particular treatment protocols can be analyzed for specific mutations and a correlation can be established according to the methods provided herein. Alternatively, patients who respond poorly to a particular treatment regimen can also be analyzed for particular mutations correlated with the poor response. Then, a subject who is a candidate for treatment for CAKUT can be assessed for the presence of the appropriate mutation(s) and a targeted treatment regimen can be provided. In some embodiments, the methods of correlating a mutation(s) with treatment regimens can be carried out using a computer database.

Thus, some embodiments provide a computer-assisted method of identifying a proposed treatment for CAKUT.

Example Embodiments

The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N. Y. (2000). Unless defined otherwise, all technical and scientific terms used herein have the same meaning as commonly understood by one of ordinary skill in the art.

Various example embodiments are described in the figures. The following is a summary of results of experiments described within the examples.

(i) Genome-wide analysis of linkage using affected-only analysis identified five regions of the genome that were shared among all seven affected subjects.

(ii) Whole exome sequencing identified a single rare deleterious variant within linkage intervals—a heterozygous splice-site mutation in DSTYK—which results in aberrant gene product splicing and was present in all affected family members.

(iii) Sanger sequencing detected two SNVs in all affected individuals and the obligate carrier in K100: (p.A111V) in TIMM17A and (c.654+1 G>A) in DSTYK. The latter was absent in controls.

(iv) All mutation carriers harbor a heterozygous 27 pb deletion resulting from use of an alternative splice donor within the normal exon 2, which would produce a nine amino acid in-frame deletion (VTMHHALLQ, SEQ ID NO: 7) in a domain that is highly conserved among mammals.

(v) Five additional novel damaging DSTYK variants in 7 of 311 (2.2%) unrelated CAKUT patients were identified.

(vi) DSTYK is ubiquitously expressed and localizes to cell membranes of major organs.

(vii) Morpholino knock-down in Zebrafish results in multi-organ development defects including growth retardation as evidenced by small fins, abnormal tail morphogenesis and loss of heartbeat, cloacal malformations, defects in jaw development, loss of median fin fold, and pericardial effusion.

(viii) DSTYK colocalizes with fibroblast growth factor (FGF) receptors in developing and adult kidney and mediates FGF signaling, and siRNA knockdown of DSTYK in HEK293 cell lines resulted in abrogation of ERK phosphorylation, which is a key signaling transduction event downstream of FGF signaling.

FIG. 1A is a diagram that illustrates example DSTYK mutations in a family with CAKUT according to an embodiment. This family is designated K100 and parents are above children, sibling on the same horizontal line. Black-filled symbols=individuals expressing CAKUT; white symbols=individuals not expressing CAKUT; gray-filled symbols=phenotype unknown. Black-filled dot superscript indicates a DSTYK mutation carrier. 21 individuals are mapped in this family K100.

Genetic linkage is the tendency of genes that are located proximal to each other on a chromosome to be inherited together during meiosis. Genes whose loci are nearer to each other are less likely to be separated onto different chromatids during chromosomal crossover, and are therefore said to be genetically linked. FIG. 1B is a diagram that illustrates example linkage analysis that identifies five linked regions of the genome, according to an embodiment. The horizontal axis 112 indicates genetic distance across the genome, organized into the 22 chromosomes. The lengths of the labeled chromosomes represent the distance encompassed by each chromosome, with each plotted point indicating one gene. The vertical axis 114 indicates the logarithm of odds (LOD) score and is dimensionless. The LOD score compares the likelihood of obtaining the test data if two loci are indeed linked, to the likelihood of observing the same data purely by chance. Positive LOD scores favor the presence of linkage, whereas negative LOD scores indicate that linkage is less likely. Computerized LOD score analysis is a simple way to analyze complex family pedigrees in order to determine the linkage between Mendelian traits (or between a trait and a marker, or two markers). Trace 116 indicates the linkage analysis, which identifies five regions (indicated by arrows 117) of the genome reaching the maximal expected LOD score of 1.5. DSTYK is located in the chr. 1q25-41 locus marked by the interval 118. This genome-wide analysis of linkage using affected-only analysis identified five regions of the genome that were shared among all seven affected subjects. One of the five regions is the DSTYK gene. These intervals collectively spanned 55.44 Megabases (Mb, 1 Mb=106 bases), which is ~1.8% of the genome, containing 645 protein-coding genes.

CNV analysis in all affected individuals excluded major genomic imbalances. Whole exome sequencing, conducted in individuals 13 and 20 at a mean depth of 108×, identified 14,943 single nucleotide variants (SNVs) across the genome, including 709 SNVs absent in all public databases. Among these, there were 24 protein-altering variants that were shared by the two affected subjects (missense/nonsense/splice site variants. Of these, only two SNVs, both on Chr. 1q25-41, mapped to the five linkage intervals. Follow-up by Sanger sequencing detected both SNVs in all affected individuals and the obligate carrier in K100. One of these SNVs (p.A111V in TIMM17A) was common among Sardinians (MAF=0.47). The other variants, a canonical splice donor SNV at the $1^{st}$ base following exon 2 (c.654+1 G>A) of DSTYK was absent in 48 Sardinian and 384 European controls matched for recruitment site. The DSTYK mutation was heterozygous in all affected individuals, obligate carriers and two apparently unaffected members of K100.

Figure 1C:
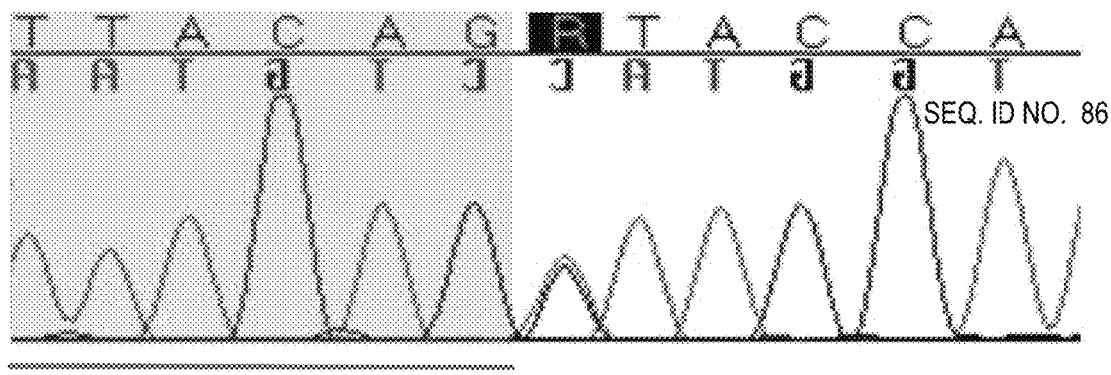
FIG. 1C (SEQ ID NOS: 86 and 87) is a diagram that illustrates an example chromatogram of a first DSTYK mutation in genomic deoxyribonucleic acid (DNA), according to an embodiment.

FIG. 1C is a diagram that illustrates an example chromatogram of a first DSTYK mutation in genomic deoxyribonucleic acid (DNA), according to an embodiment. This illustrates the DSTYK c.654+1 G>A mutation at the first intron location, which leads to a splicing alternative that deletes 27 base pairs from exon 2. The reverse sequence is the read on the reverse strand (the sequence is the complementary sequence, with the complementary nucleotide is shown, e.g. C instead of G, or A instead of T. In various figures, the labels R, K etc. are International Union of Pure and Applied Chemistry (IUPAC) codes for two or more nucleotides being read at the same position due to heterozygosis at that position or a frame shift mutation, which is the case in FIG. 1C. For example, Y represents any pyrimidine, and R indicates any purine. The full set is given in Table 5. The resulting sequence is shown in Table 2 and FIG. 1D.

Figure 1D:
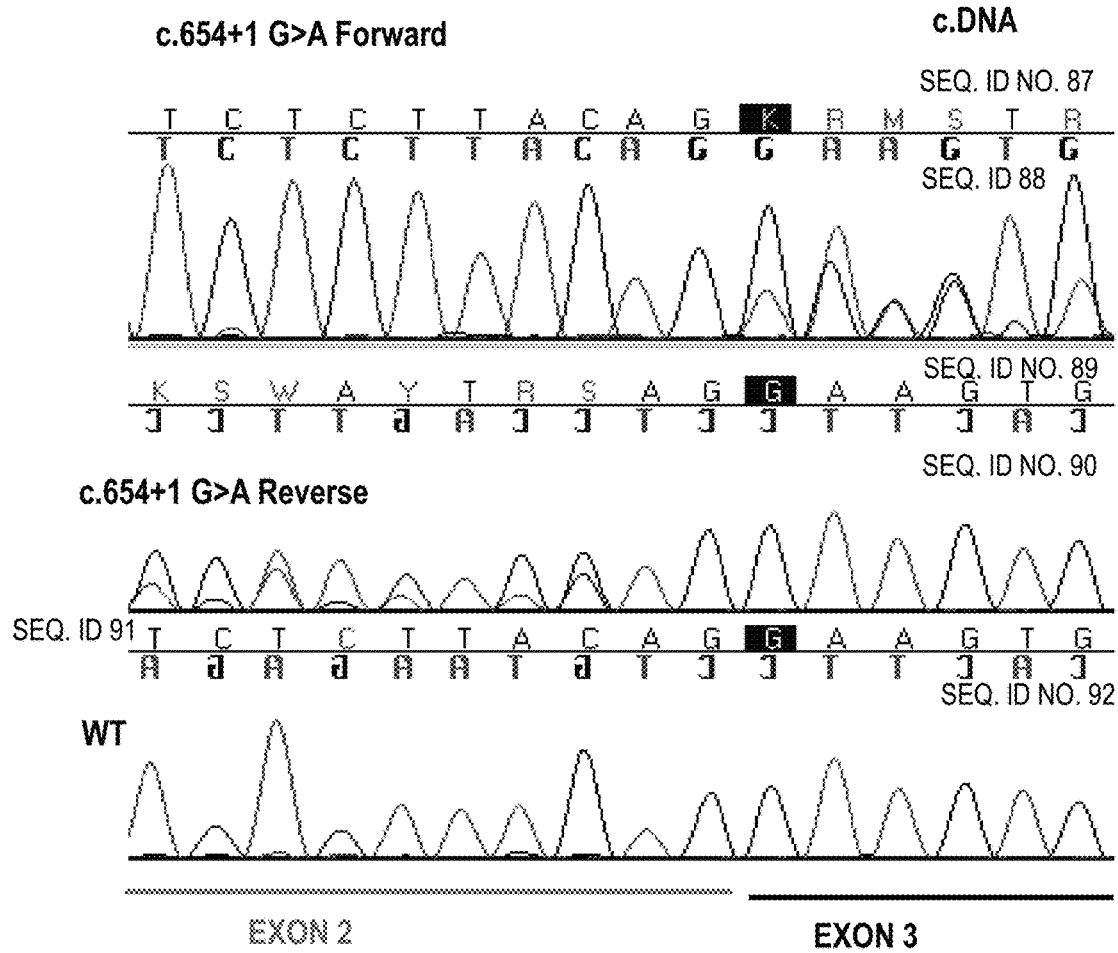
FIG. 1D (SEQ ID NOS: 88-94) is a diagram that illustrates example complementary DNA (cDNA) demonstrating an alternative splice site in exon 2 in mutation carriers, leading to a 27 base pair base pair (bp) deletion, according to an embodiment.

FIG. 1D is a diagram that illustrates example complementary DNA (cDNA) demonstrating an alternative splice site in exon 2 in mutation carriers, leading to a 27 base pair base pair (bp) deletion, according to an embodiment. The upper chromatogram is mapped in the forward phase and the middle chromatogram in the reverse phase. The lower chromatogram indicates the wild type (reference) sequence (SEQ ID 93) in this portion of the DTSYK gene. A longer section of the wild type (reference) sequence is shown below the chromatograms as SEQ ID NO: 93. The 27 base pairs deleted are indicated by the converging lines beginning at the cryptic splice site to the shortened sequence (SEQ ID NO: 1).

TABLE 5

Symbols for degenerate nucleotide bases.

| symbol | description | Number of bases | Bases represented |
|---|---|---|---|
| W | weak | 2 | A, T |
| S | strong | 2 | C, G |
| M | amino | 2 | A, C |
| K | keto | 2 | G, T |
| R | purine | 2 | A, G |
| Y | pyrimidine | 2 | C, T |
| B | not A | 3 | C, G, T |
| D | not C | 3 | A, G, T |
| H | not G | 3 | A, C, T |
| V | not T or U | 3 | A, C, G |
| N (or —) | any | 4 | A, C, G, T/U |

Figure 1E:
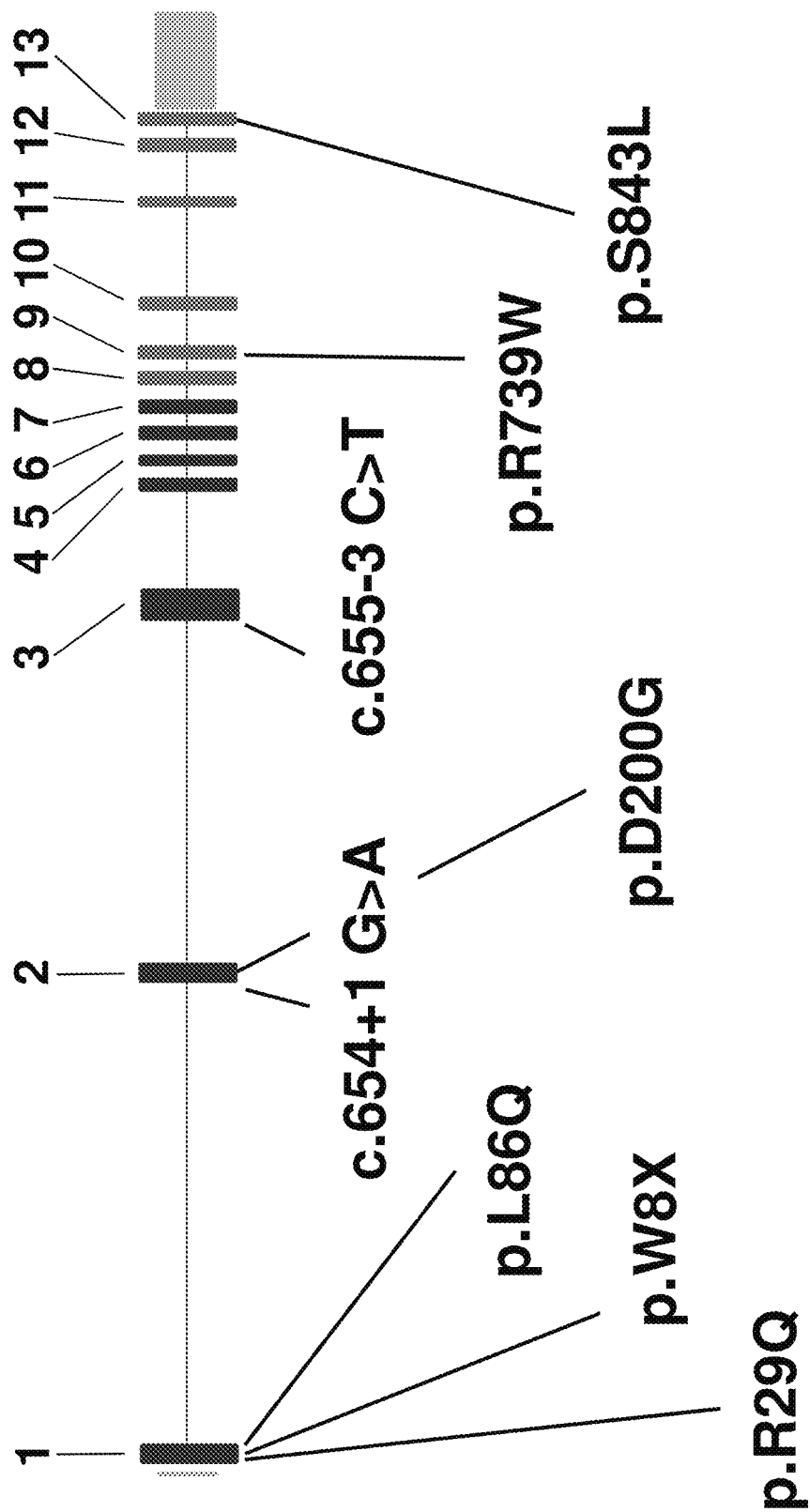
FIG. 1E is a diagram that illustrates example genomic structure of DSTYK and location of pathogenic mutations in additional CAKUT cases, according to an embodiment.

FIG. 1E is a diagram that illustrates example genomic structure of DSTYK and location of pathogenic mutations in additional CAKUT cases, according to an embodiment. The exons are indicated by the thick bars numbered 1 through 13 separated by introns. Exons 8 through 13 encode the kinase domain. FIG. 1E includes two common variants p.L86Q and p.R739W, not yet demonstrated to be causative for CAKUT. As demonstrated in FIG. 1E, protein mutations p.W8X, p.R29Q and p.L86Q occur in exon 1. The genomic DNA mutation c.654+1G>A occurs at exon 2 (the +1 notation indicates the first bp in intron following exon 2), which leads to deleting 27 base pairs from exon 2. Protein mutation p.D200G occurs in exon 2. The cDNA mutation c.655-3C>T occurs at exon 3 (the -3 notation indicate three bp in intron before exon 3). Protein mutation p.R739W occurs in exon 9; and, protein mutation p.S843L occurs in exon 13.

Figure 1F:
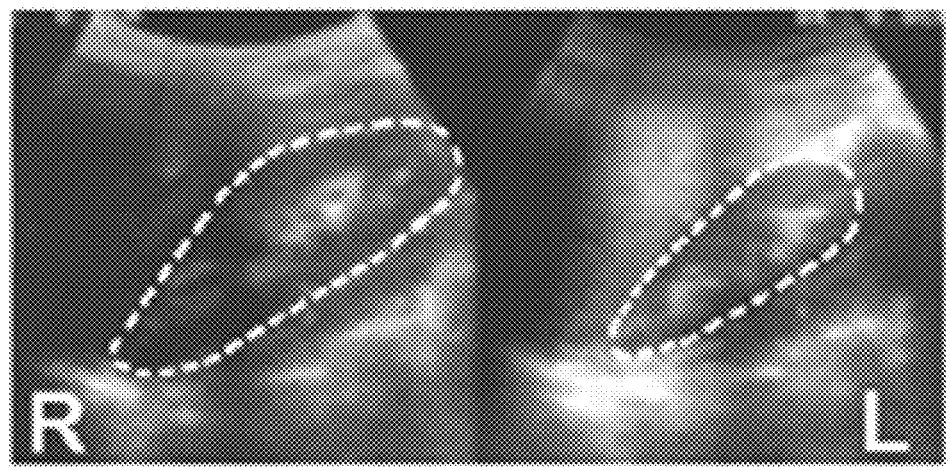
FIG. 1F through FIG. 1I are ultrasound images that illustrate example malformations associated with DSTYK mutations, according to various embodiments.
Figure 1G:
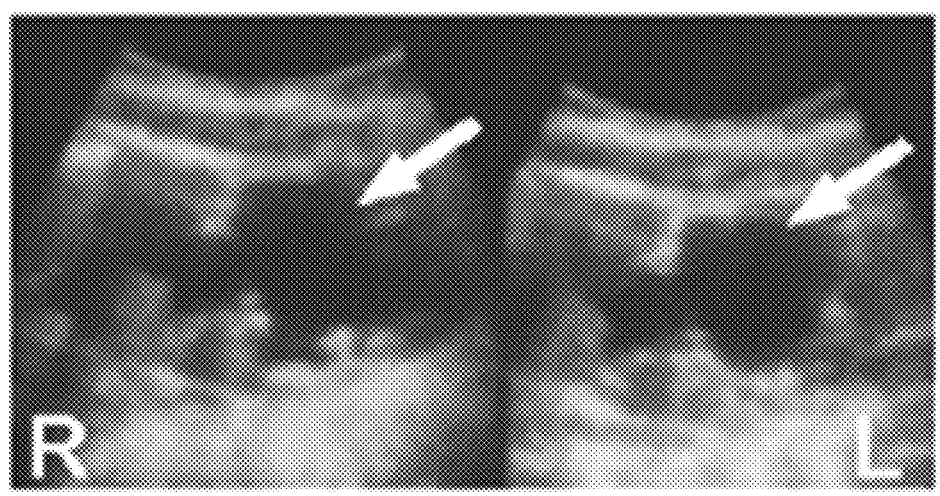
Figure 1H:
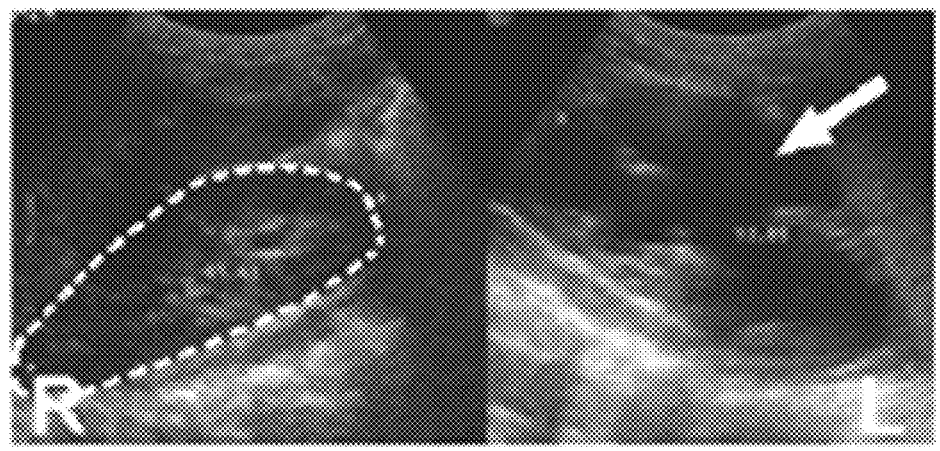
Figure 1I:
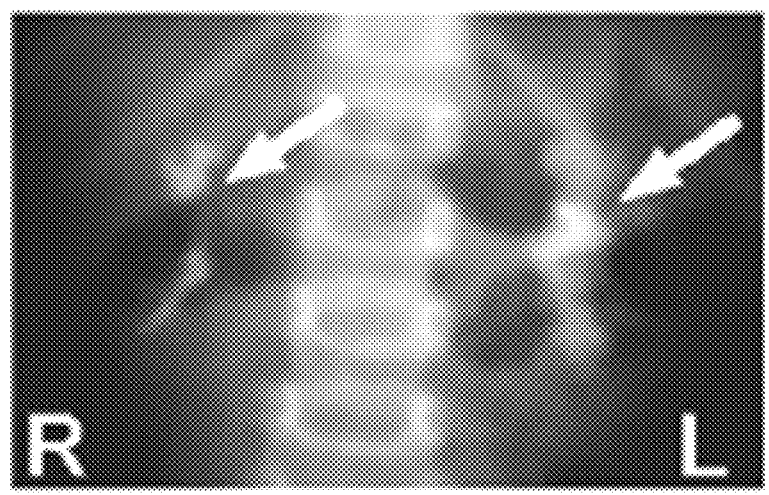

FIG. 1F through FIG. 1I are ultrasound images that illustrate example malformations associated with DSTYK mutations, according to various embodiments. FIG. 1F illustrates ultrasound windows of the maximal length of each kidney for right (R) and left (L) side; and, shows left-sided renal hypoplasia detected at birth in a girl with p.R29Q mutation. The kidneys are outlined by the dashed lines. FIG. 1G illustrates ultrasound windows for right (R) and left (L) sides; and, shows bilateral hydronephrosis (arrows) secondary to UPJO detected at birth in girl with a c.655-3 C>T mutation. FIG. 1H illustrates ultrasound windows for right (R) and left (L) sides; and, shows left-sided hydronephrosis (arrow) secondary to UPJO detected in a 5-year old boy with p.R29Q mutation. The right kidney, outlined by the dashed lines, is normal in size. FIG. 1I illustrates intravenous pyelography for right (R) and left (L) sides, showing right-sided blunting of fornices and left-sided calyceal dilatation in a 2-year-old boy with a p.W8X mutation.

DSTYK has a striking membrane-associated distribution in mesenchymal-derived cells of all major organs. In the developing mouse kidney, it is expressed at low levels in the nephrogenic zone but is more highly expressed in maturing tubular epithelia, with the most prominent expression in the medulla and the papilla. In the postnatal mouse and human pediatric kidney, DSTYK is detected in the basolateral and apical membranes of all tubular epithelia. It has both basolateral and cytoplasmic distribution in the thin ascending limb of the loop of Henle and the distal convoluted tubule, but expression is restricted to apical and basolateral membranes in the collecting duct, including principal and intercalated cells.

Figure 2A:
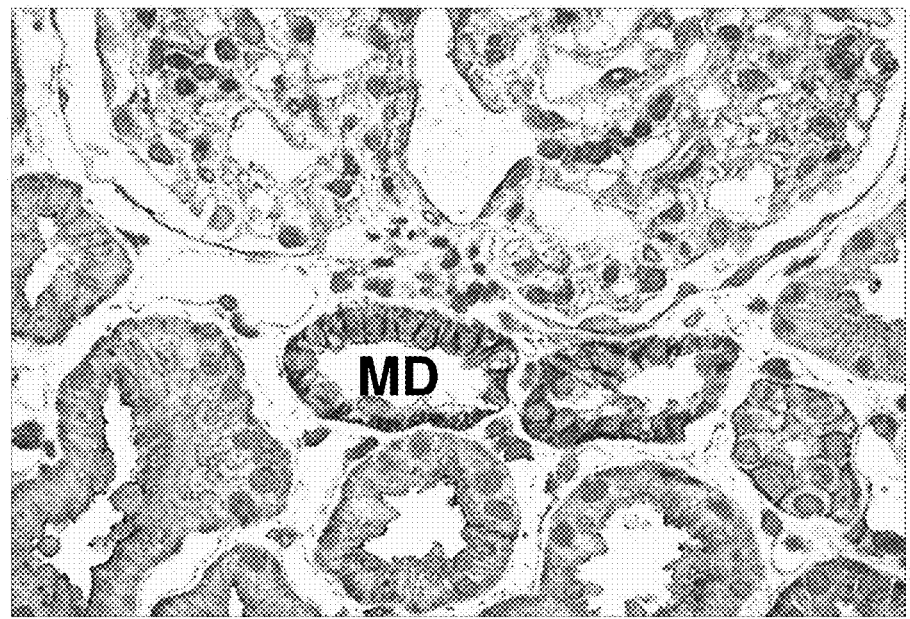
FIG. 2A through FIG. 2D are stained microscopy images showing example DSTYK expression in human pediatric (3 months old) kidney and ureter, according to an embodiment.
Figure 2B:
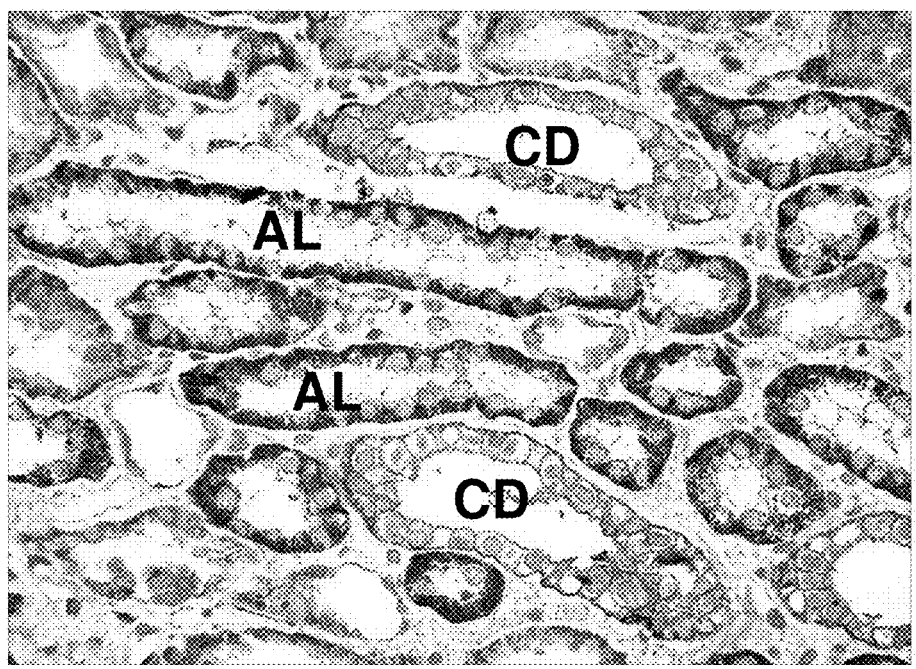
Figure 2C:
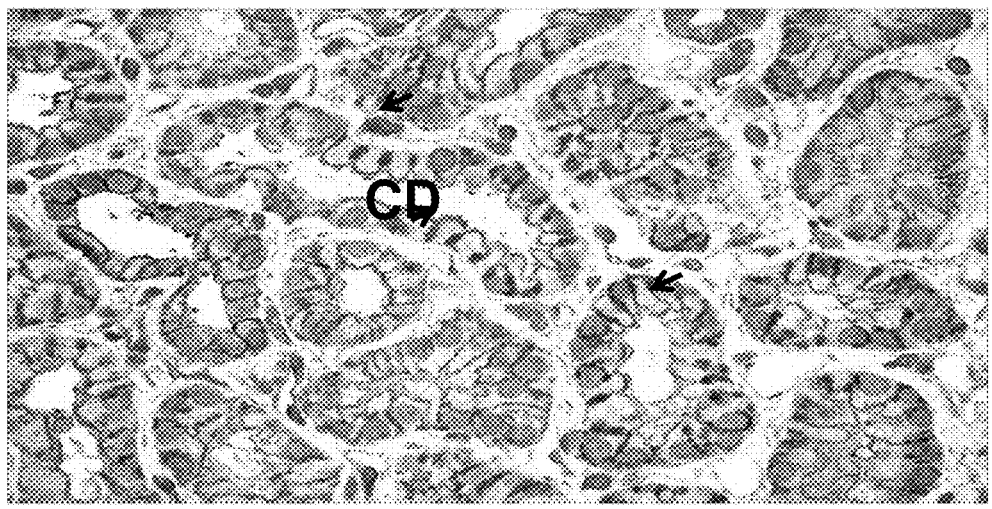

FIG. 2A through FIG. 2D are stained microscopy images showing example DSTYK expression in human pediatric (3 months old) kidney and ureter, according to an embodiment. FIG. 2A shows a kidney glomerulus and Macula densa (MD) magnified at 600 times (600×). FIG. 2B shows a renal cortex at 400× showing ascending limb of loop of Henle (AL) and Collecting duct (CD). FIG. 2C shows a renal medulla at 400 C showing collecting duct (CD), with punctate staining at basolateral side (arrow).

Figure 2D:
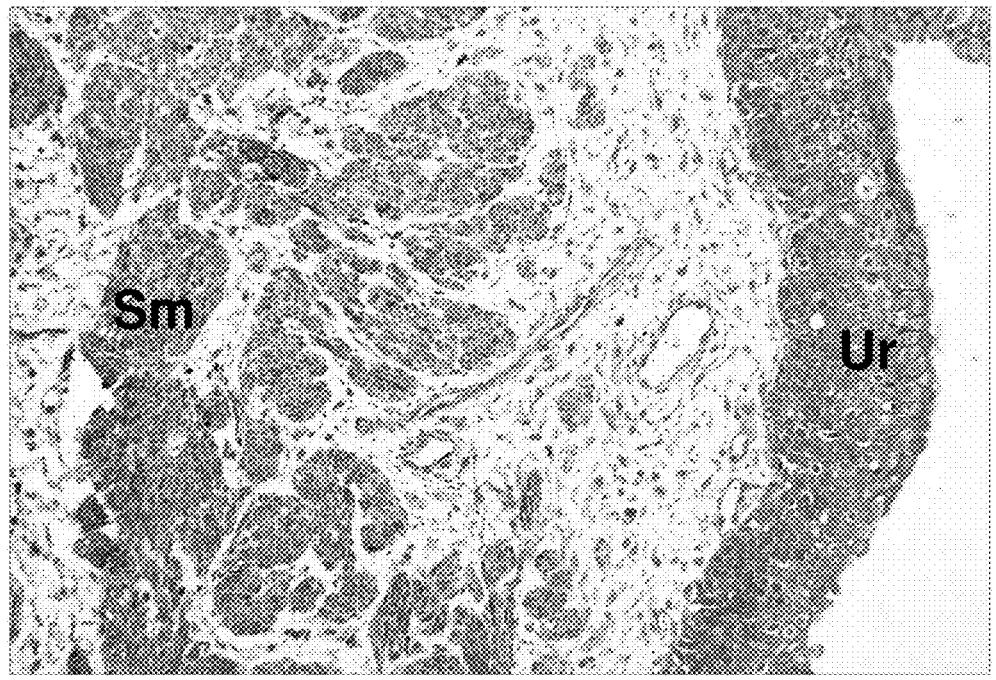

FIG. 2D shows a ureter at 200× with urothelium (Ur) and smooth muscle layer (Sm). DSTYK was detected in all layers of transitional ureteric epithelium and in the ureteric smooth muscle cells.

Figure 2E:
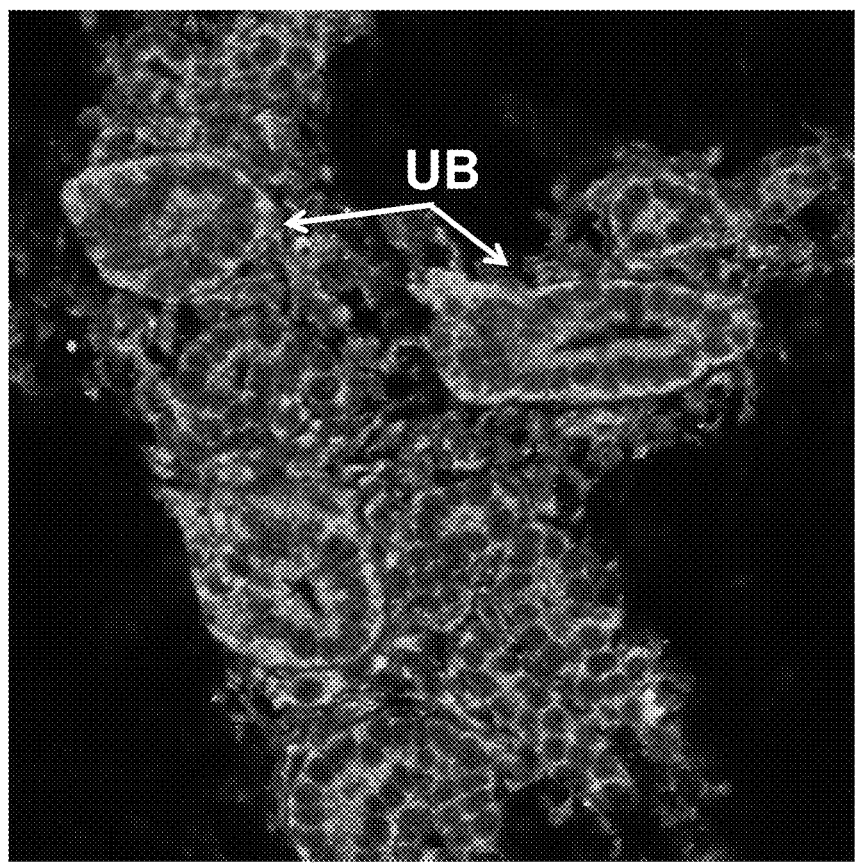
FIG. 2E through FIG. 2H are fluorescent stained microscopy images showing example DSTYK colocation with FGF receptors, according to an embodiment.
Figure 2F:
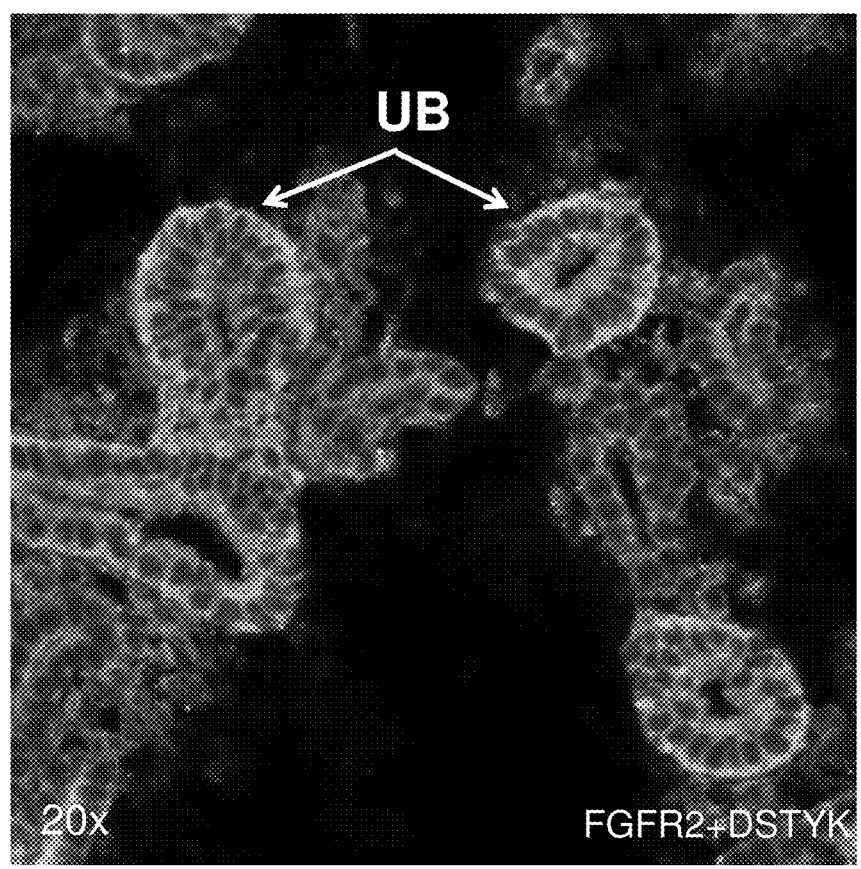
Figure 2G:
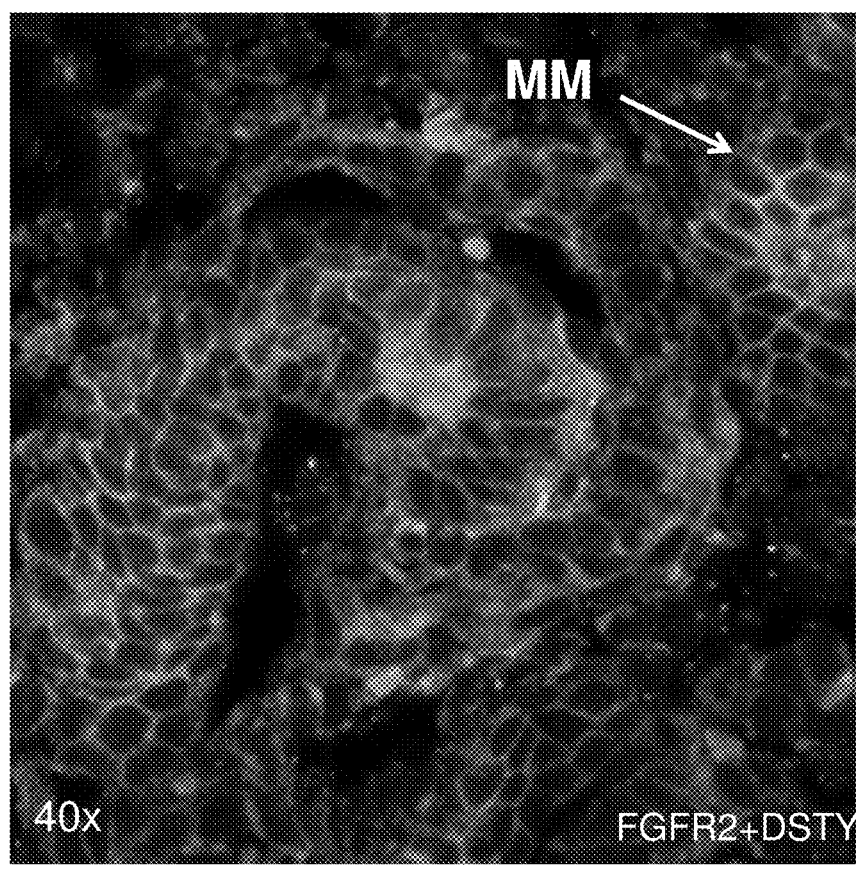
Figure 2H:
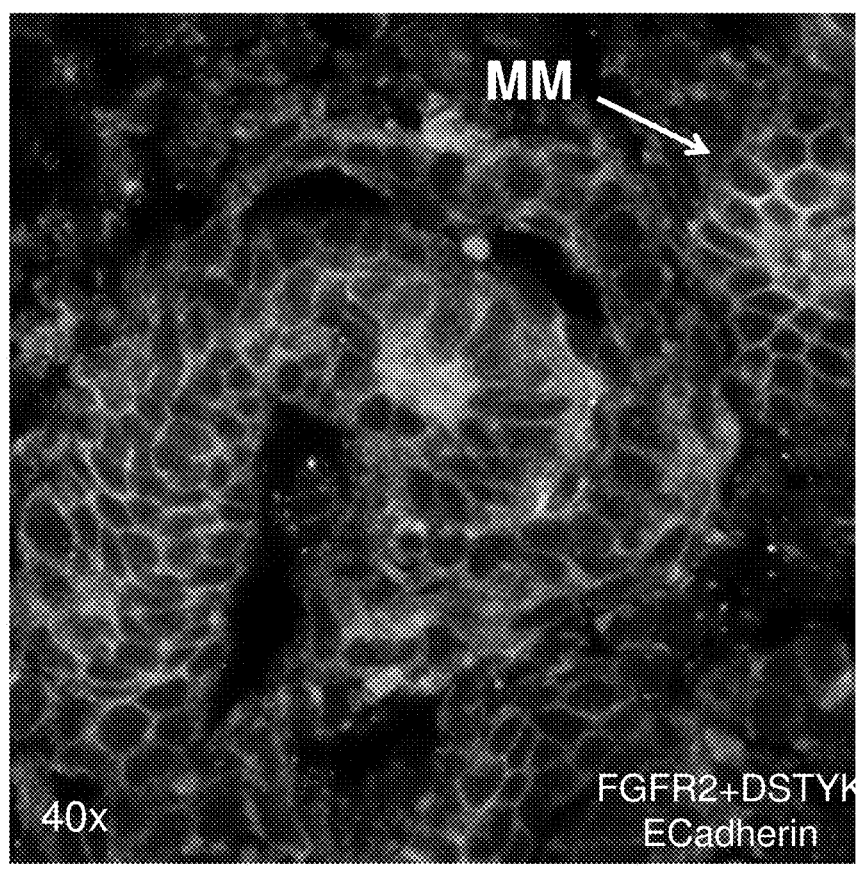

FIG. 2E through FIG. 2H are fluorescent stained microscopy images showing example DSTYK colocation with FGF receptors, according to an embodiment. Immunofluorescence analysis is used in developing murine kidney. FIG. 2E shows DSTYK colocalization with FGFR1. UB indicates ureteric bud. FIG. 2F and FIG. 2G shows DSTYK colocalization with FGFR2 FIG. 2H shows DSTYK colocalization with and E-cadherin where MM indicates metanephric mesenchyme.

In the developing nephron, DSTYK colocalizes with E-cadherin positive and negative cells, confirming that DSTYK is expressed both in the metanephric mesenchyme (MM) and the ureteric bud (UB). DSTYK localization to cell membrane in the MM and UB highly parallels the known expression pattern of FGF receptors. Consistent with this prediction, DSTYK colocalizes with both FGFR1 and FGFR2 in the UB and comma-shaped bodies. Co-localization with FGFR2 was also evident in distal tubular cells in the adult renal medulla and papilla. Punctate DSTYK staining was seen at apical cell-cell junctions lining ureteric bud epithelia.

Upon activation, FGF receptors trigger cytoplasmic protein kinases, resulting in phosphorylation of extracellular-signal-regulated kinase (ERK), which is the main effector of FGF-induced transcriptional activity.17,18 Because DSTYK encodes a kinase and colocalizes with FGFR1 and FGFR2, it is hypothesized that DSTYK acts as a positive regulator of FGF-mediated signaling in the kidney.

Figure 2I:
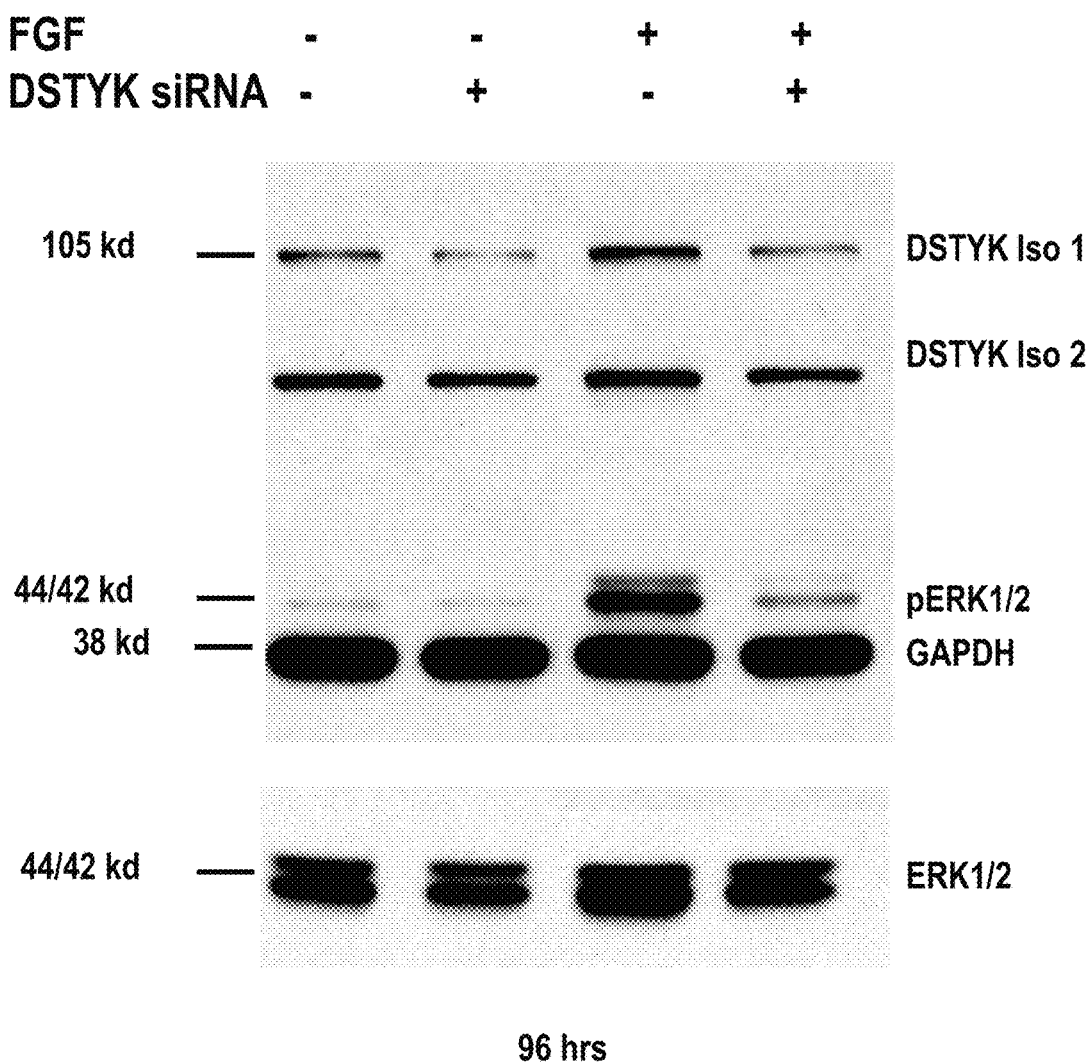
FIG. 2I is a photograph that illustrates example western blot data that indicates example DSTYK knockdown inhibits FGF-mediated extracellular-signal-regulated kinase (ERK) phosphorylation at 96 hours post knockdown, according to an embodiment.

To test this hypothesis, siRNA knockdown of DSTYK was performed. FIG. 2I is a photograph that illustrates example western blot data that indicates example DSTYK knockdown inhibits FGF-mediated extracellular-signal-regulated kinase (ERK) phosphorylation at 96 hours post knockdown, according to an embodiment (+ means present, – means absent). The amounts of ERK1/2 and GAPDH appear to be unaffected by + and – changes. In contrast, knocking down DSTYK with siRNA, when combined with stimulation for FGF increases phosphorylated ERK1/2 (pERK1/2) and DSTYK 1.

Figure 2J:
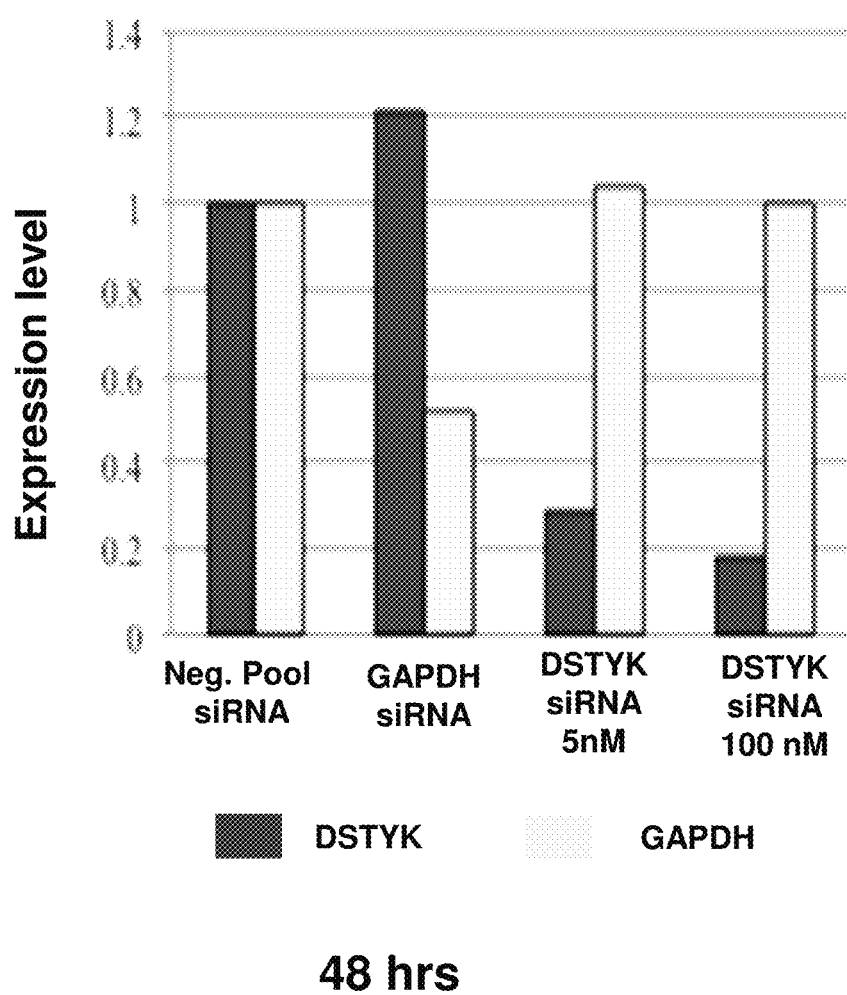
FIG. 2J is a bar graph that illustrates example transcript level by qPCR for knock down of DSTYK in T cells, according to an embodiment.

Up to 80% reduction of transcript levels and pronounced reduction of DSTYK protein levels resulted by 96 hours post-transfection. Furthermore, FGF stimulation augmented diphospho-ERK levels as expected, but siRNA silencing of DSTYK significantly prevented ERK phosphorylation. This effect was not mediated by a direct physical interaction of DSTYK with FGFR2. Combined with co-localization of DSTYK with FGFR1 and FGFR2, these data implicate DSTYK downstream of FGF signaling FIG. 2J is a bar graph that illustrates example transcript level by qPCR for knock down of DSTYK in T cells, according to an embodiment. The vertical axis indicates the expression level of a cDNA sequence for the protein as determined by quantitative Polymerase Chain Reaction (qPCR). The amounts of both DSTYK and GAPDH are equal with no small interfering RNA (Neg. Pool siRNA). The value of GAPDH is greatly reduced to about 50%, with GAPDH siRNA as shown in the second column. The value of DSTYK is greatly reduced to about 30% with 5 nano-Molar (nM, 1 nM=$10^{-9}$ Molar) DSTYK siRNA as shown in the third column; and, reduced even more to about 20% with 100 nM DSTYK siRNA as shown in the fourth column. Transcript levels for DSTYK knockdown using siRNA targets (SEQ ID NOS: 98-101), as determined by quantitative PCR (qPCR), are reduced to 20% of control values.

Expression analysis of DSTYK by immunohistochemistry in mouse embryo at e18.5 demonstrates membrane associated expression in all tissues, including heart, lung, liver, colon, salivary gland, skin, kidney nephrogenic zone, kidney medulla and kidney papilla. DSTYK as a membrane-associated distribution is expressed in all tubules. Prominent basolateral distribution is found in the collecting duct. Expression is shown in ascending loop of Henle and CD. DSTYK is expressed in the renal papillary cells, with prominent apical and basolateral distribution; and in the ureteric epithelim.

Co-staining of DSTYK with aquaporin2 (AQ2) in adult mouse medulla and papilla indicates that DSTYK is expressed in both principal and intercalated cells (IC), which are aquaporin positive and negative, respectively.

Morpholino-induced knock-down of DSTYK is demonstrated in zebrafish embryos. At 26 hours past transfection (hpf), control zebrafish embryos have developed a straight body axis and fin fold. In contrast, DSTYK morphants show absence of fin development, undulating body axis and deformed notochord. At 48 hpf, DSTYK morphants show developmental retardation with compressed somites, axis curvature, absence of ventral fin, and cloacal malformation. Higher magnification view of normal and DSTYK morphant cloaca show in some cases absence of patent pronephric opening. Jaw development defects seen in DSTYK morphants are similar to what is seen in embryos defective in FGF signaling. At five days surviving DSTYK morphants show severe edema that can be ascribed to combined cardiac and kidney failure. Similar results were obtained generating DSTYK morphants in wild-type and p53 mutant zebrafish.

Immunofluorescence analysis in developing murine kidney shows DSTYK colocalization with E-cadherin at E12.5 DSTYK also colocalizes with FGFR2 at E15.5. Immunofluorescence analysis shows that DSTYK co-localizes with FGFR2 in the adult medulla and papilla.

Superior (horizontal) and lateral (vertical) images were formed by maximum-intensity projection from confocal z-stack images. Crosshairs intersect at the basolateral surface of a developing comma-shaped body (MM-derived) for punctate DSTYK staining (vertical z projection). Punctate DSTYK staining is seen maximally at apical cell-cell junctions lining ureteric bud epithelia (*in lumen and in horizontal z projection).

Co-immunoprecipitation with anti-FGFR2 antibodies does not show complex formation between FGFR2 and DSTYK. 293Tcell lysates (lanes 3 and 6) were immunoprecipitated with rabbit anti-FGFR2 antibodies (lanes 1 and 4) or with control rabbit IgG (lanes 2 and 5) and the samples were subjected to western blot analysis using polyclonal anti-FGFR2 antibodies (lanes 1-3) or goat anti-DSTYK antibodies (lanes 4-6). Despite very efficient precipitation of FGFR2 (lane 1) and high level of DSTYK in the lysate (lane 6), there was no evidence DSTYK was co-immunoprecipitated after FGFR2 precipitation (lane 4).

Implications for Cancer Treatment

As noted above, inhibition of DSTYK will abrogate FGF signaling and can therefore be beneficial in situations where elevated FGF signaling promotes disease pathology, such as solid tumor growth and angiogenesis. For example, a focal region encompassing the FGF receptor type 1 (FGFR1) is frequently amplified in lung cancer (Peifer, 2012 #5589; Weiss, 2010 #5588) and FGF receptor type 2 (FGFR2) is frequently mutated in endometrial cancer (Dutt, 2008 #5591; Pollock, 2007 #5590). Inhibition of DSTYK was accomplished, as described above, using siRNA. Such inhibition reduces FGF signaling and provides a treatment method for such cancers. Inhibition of DSTYK expression at the gene transcription and mRNA translation levels can be accomplished using siRNA or other inhibitory oligonucleotides that hybridize with the gene or mRNA thereby blocking transcription or translation, as is described below.

Dysregulation of FGF signaling in cancer is now well understood and it is becoming increasingly likely that certain tumors become dependent on activation of this pathway for their growth and survival. Preclinical studies have shown that dysregulation of FGFR-dependent signaling can contribute to tumor growth and angiogenesis through a variety of mechanisms. Nigel Brooks, et al., Clin Cancer Res, published OnlineFirst Mar. 2, 2012. For example, a focal region encompassing the FGF receptor type 1 (FGFR1) is frequently amplified in lung cancer (Peifer, 2012 #5589; Weiss, 2010 #5588) and FGF receptor type 2 (FGFR2) is frequently mutated in endometrial cancer (Dutt, 2008 #5591; Pollock, 2007 #5590). Gene amplification of FGFR1 also occurs in estrogen receptor (ER)-positive breast cancer, and FGFR2 amplification occurs in diffuse-type gastric cancer and triple-negative breast cancer. Chromosomal translocation of FGFR1 occurs in the 8p11 myeloproliferative syndrome and alveolar rhabdomyosarcoma, as with FGFR3 in multiple myeloma and peripheral T-cell lymphoma. FGFR1 and FGFR3 genes are fused to neighboring TACC1 and TACC3 genes, respectively, due to interstitial deletions in glioblastoma multiforme. Missense mutations of FGFR2 are found in endometrial uterine cancer and melanoma; similar FGFR3 missense mutations occur in invasive bladder tumors, and FGFR4 missense mutations in rhabdomyosarcoma. Katoh, M., Med Res Rev. 2014 March; 34(2):280-300; FGF receptors: cancer biology and therapeutics. Inhibition of DSTYK expression by blocking transcription or translation will therefore reduce FGF signaling and have therapeutic utility in treating these cancers. A number of MAP kinases downstream of FGF signaling have been targeted for treatment of cancer due to overexpression of FGF pathway (e.g. Motzer et al., Lancet Oncol. 2014 March; 15(3):286-96, Tater et al., Blood. 2014 March 6; 123(10): 1516-24, Brooks et al., Clin Cancer Res. 2012 Apr. 1; 18(7):1855-62). Similarly, it is anticipated that inhibition of DSTYK will enable abrogation of FGF signaling in solid and hematogenous tumors driven by overexpression of FGF and FGF receptors.

Materials and Methods
Screening for DSTYK Gene Mutations

In some embodiments, screening for or diagnosing CAKUT, or a predisposition or risk of developing CAKUT in a subject is now possible by detecting the presence of a DSTYK mutation in a subject. Numerous methods are known in the art for determining the presence of a mutation in a biological sample. For example, methods of detecting point mutations may be accomplished by molecular cloning of the specified allele and subsequent sequencing of that allele using techniques well known in the art such as Sanger sequencing or massively parallel ("Next Gen") sequencing of the of the coding regions and flanking introns of the DSTYK gene. A method according to some embodiments can identify the DSTYK gene mutation on either strand of DNA. Additionally, the gene sequences may be amplified directly from DNA or mRNA (or on other nucleic acid sequences, such as cDNA) samples using well-known amplification techniques such as PCR, and the sequence can then be determined from the amplified product.

The nucleic acid sample may be obtained from any part of the subject's body, including, but not limited to hair, skin, nails, tissues or bodily fluids such as saliva and blood. Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., 1989, Molecular Cloning: A Laboratory Manual, Cold Spring Harbor Laboratory, New York, incorporated herein by reference.

Nucleic acid isolation protocols are well known to those of skill in the art. For example, an isolated polynucleotide corresponding to a gene or allele or chromosome region may be prepared according to the following procedure: (a) creating primers which flank an allele or transcript thereof, or a portion of the allele or transcript; (b) obtaining a nucleic acid extract from an individual affected with, or at risk of developing CAKUT and (c) using the primers to amplify, via nucleic acid amplification techniques, at least one amplification product from the nucleic acid extract, wherein the amplification product corresponds to the allele or transcript linked to the development of the condition.

Optionally, the nucleic acid samples obtained from the subject are amplified prior to detection. The term "nucleic acid" refers to a deoxyribonucleotide or ribonucleotide, whether singular or in polymers, naturally occurring or non-naturally occurring, double-stranded or single-stranded, coding (e.g. translated gene) or non-coding (e.g. regulatory region), or any fragments, derivatives, mimetics or complements thereof. Examples of nucleic acids include oligonucleotides, nucleotides, polynucleotides, nucleic acid sequences, genomic sequences, antisense nucleic acids, DNA regions, probes, primers, genes, regulatory regions, introns, exons, open-reading frames, binding sites, target nucleic acids and allele-specific nucleic acids. A nucleic acid can include one or more polymorphisms, variations or mutations (e.g., SNPs, insertions, deletions, inversions, translocations, etc.). A nucleic acid includes analogs (e.g., phosphorothioates, phosphoramidates, methyl phosphonate, chiral-methyl phosphonates, 2-O-methyl ribonucleotides) or modified nucleic acids (e.g., modified backbone residues or linkages) or nucleic acids that are combined with carbohydrates, lipids, protein or other materials, or peptide nucleic acids (PNAs) (e.g., chromatin, ribosomes, transcriptosomes, etc.) or nucleic acids in various structures (e.g., A DNA, B DNA, Z-form DNA, siRNA, tRNA, ribozymes, etc.).

Target nucleic acids are amplified to obtain amplification products. Typically DNA sequences are amplified, although in some instances RNA sequences can be amplified or converted into cDNA, such as by using RT PCR. "cDNA" or "complementary DNA" is DNA synthesized from a messenger RNA (mRNA) template in a reaction catalyzed by the enzyme reverse transcriptase and the enzyme DNA polymerase. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

A reverse transcriptase PCR™ amplification procedure may be performed when the source of nucleic acid is fractionated or whole cell RNA. Methods of reverse transcribing RNA into cDNA are well known (see Sambrook et al., 1989). Alternative methods for reverse polymerization utilize thermostable DNA polymerases. These methods are described in WO 90/07641. Representative methods of RT-PCR are described in U.S. Pat. No. 5,882,864.

Suitable nucleic acid amplification techniques are well known to a person of ordinary skill in the art, and include polymerase chain reaction (PCR) as for example described in Ausubel et al., Current Protocols in Molecular Biology (John Wiley & Sons, Inc. 1994-1998) (and incorporated herein) strand displacement amplification (SDA) as for example described in U.S. Pat. No. 5,422,252; rolling circle replication (RCR) as for example described in Liu et al., (1996, J. Am. Chem. Soc. 118: 1587-1594 and International application WO 92/01813) and Lizardi et al., (International Application WO 97/19193); nucleic acid sequence-based amplification (NASBA) as for example described by Sooknanan et al., (1994, Biotechniques 17: 1077-1080); ligase chain reaction (LCR); simple sequence repeat analysis (SSR); branched DNA amplification assay (b-DNA); transcription amplification and self-sustained sequence replication; and Q-13 replicase amplification as for example described by Tyagi et al., (1996, Proc. Natl. Acad. Sci. USA 93: 5395-5400).

Primers may be manufactured using any convenient method of synthesis. Examples of such methods may be found in "Protocols for Oligonucleotides and Analogues; Synthesis and Properties," Methods in Molecular Biology Series; Vol. 20; Ed. Sudhir Agrawal, Humana ISBN: 0-89603-247-7; 1993. The primers may also be labeled to facilitate detection.

The primer may be any one of the above, so long as it is capable of amplifying at least a part of the coding region of DSTYK gene or a region regulating expression thereof. Such a region includes, for example, the exon region, the intron region, the promoter region and the enhancer region of the DSTYK gene.

Similarly, oligonucleotide probes are synthetic, and generally consist of at least 15 bases or more. The region used as a probe can be any region so long as it hybridizes specifically to at least a part of the coding region of the DSTYK gene comprising the mutations described herein, or part of the coding region of DSTYK gene generally if screening for new mutations, or the region regulating expression of DSTYK gene. Such a region of the whole gene to which the probe hybridizes includes, for example, the exon region, the intron region, the promoter region and the enhancer region of the DSTYK gene.

Probes such as oligonucleotides, double-stranded DNAs, and RNAs can be used with proper labels. Labeling methods include, for example, end labeling for oligonucleotides, random primer labeling or PCR method for double-stranded DNAs, and in-vitro transcription labeling for RNAs. Compounds useful for labeling include [γ-$^{32}$P]ATP for end labeling, [α-$^{32}$P] dCTP or digoxigenin (DIG)-dUTP for random primer labeling and PCR method, and [α-$^{32}$P] CTP or DIG-UTP for in-vitro transcription labeling.

In some embodiments, fragments of the DSTYK gene having the six described mutations are analyzed by hybridization using one or more oligonucleotide probes specific for a region in the DSTYK gene corresponding to one or more of the six mutations selected from Table 3, and under conditions sufficiently stringent to disallow a single nucleotide mismatch. In certain embodiments, suitable oligonucleotide probes can distinguish between a normal DSTYK gene fragment and a fragment having a DSTYK gene mutation, including one or more of the six mutations selected from Table 3. For example, suitable oligonucleotide probes specifically bind to a normal DSTYK gene but not to a mutant DSTYK gene containing one or more mutations selected from Table 3. Alternatively, oligonucleotide probes can be selected that specifically bind to a mutant DSTYK gene/fragment containing one or more mutations selected from Table 3 but not to a normal DSTYK gene/or gene fragment. Oligonucleotide probes of the present embodiment include those that are capable of specifically hybridizing a mutant DSTYK allele containing one or more mutations listed in Table 3. Probes of the present embodiment also include those that are capable of specifically hybridizing a normal allele in a particular region of the DSTYK gene and therefore capable of distinguishing a normal allele from a mutant DSTYK allele containing one or more mutations listed in Table 3. Thus, for example, one of ordinary skill in the art could use probes of the embodiment to determine whether an individual is homozygous or heterozygous for a particular allele.

Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al., 1994, Current Protocols in Molecular Biology. John Wiley & Sons, Secaucus, N.J.

In some embodiments, probe molecules that hybridize to the mutant or wild-type DSTYK sequences can be used for detecting such sequences in the amplified product by solution phase or, more preferably, solid phase hybridization. Solid phase hybridization can be achieved, for example, by attaching the oligonucleotide probes to a substrate in a microchip or microarray. The microarrays comprise a solid support onto which oligonucleotide probes complementary to nucleotide fragments having one or more DSTYK mutations are attached.

Generally, oligonucleotide probes are long enough to bind specifically to a homologous region of the DSTYK gene, but short enough such that a difference of one nucleotide between the probe and the nucleic acid sample being tested disrupts hybridization. Typically, the sizes of oligonucleotide probes vary from approximately 10 to 100 nucleotides. In some embodiments, oligonucleotide probes vary from 15 to 90, 15 to 80, 15 to 70, 15 to 60, 15 to 50, 15 to 40, 15 to 35, 15 to 30, 18 to 30, or 18 to 26 nucleotides in length. As appreciated by those of ordinary skill in the art, the optimal length of an oligonucleotide probe may depend on the particular methods and/or conditions in which the oligonucleotide probe may be employed. In some embodiments, nucleic acid probes are labeled with a detectable moiety as described herein.

Screening for DSTYK Protein Mutations

Methods for detecting proteins include microscopy and protein immunostaining. Protein immunoprecipitation is a technique of precipitating a protein antigen out of solution using an antibody that specifically binds to that particular protein. Immunoelectrophoresis involves separation and characterization of proteins based on electrophoresis and reaction with antibodies. Western blot techniques couple gel electrophoresis and incubation with antibodies to detect specific proteins in a sample of tissue homogenate or extract (a type of Immunoelectrophoresis technique). Other methods include bicinchoninic acid (BCA) assay (to quantify protein concentrations) and spectrophotometry enzyme assay.

Inhibitory Oligonucleotides

Other embodiments are directed to the use of inhibitory oligonucleotides such as antisense DNA or RNA (or chimeras thereof), small interfering RNA (siRNA), micro RNA (miRNA), short hairpin RNA, ribozymes, supermir, and aptamers, to reduce or inhibit expression of the DSTYK gene or mRNA. The DSTYK mRNA and DSTYK gene sequences are set forth herein by accession numbers. Based on these known sequences, inhibitory oligonucleotides that hybridize sufficiently to the respective gene or mRNA encoding the targeted proteins to turn off expression can be readily designed and engineered using methods known in the art.

Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans. See for example Agrawal, S. and Zhao, Q. (1998) Curr. Opi. Chemical Biol. Vol. 2, 519-528; Agrawal, S. and Zhang, R. (1997) CIBA Found. Symp. Vol. 209, 60-78; and Zhao, Q, et al., (1998), Antisense Nucleic Acid Drug Dev. Vol 8, 451-458. Anderson, K. O., et al., (1996) Antimicrobial Agents Chemother. Vol. 40, 2004-2011, and U.S. Pat. No. 6,828,151 by Borchers, et al.

The oligonucleotides used herein are synthesized in vitro and do not include compositions of biological origin. Based on these known sequences of the targets (genes or mRNA) therapeutic oligonucleotides can be engineered using methods known in the art. Different combinations of these therapeutic agents can be formulated for administration to a subject using methods well known in the art.

These nucleic acids act via a variety of mechanisms. siRNA or miRNA can down-regulate intracellular levels of specific proteins through a process termed RNA interference (RNAi). Following introduction of siRNA or miRNA into the cell cytoplasm, these double-stranded RNA constructs can bind to a protein termed RNA-Induced Silencing Complex (RISC). RISC is a multiprotein complex that incorporates one strand of a small interfering RNA (siRNA) or micro RNA (miRNA). RISC uses the siRNA or miRNA as a template for recognizing complementary mRNA. When it finds a complementary strand, it activates RNase and cleaves the RNA. This process is important both in gene regulation by microRNAs and in defense against viral infections, which often use double-stranded RNA as an infectious vector RNAi can provide down-regulation of specific proteins by targeting specific destruction of the corresponding mRNA that encodes for protein synthesis.

It is desirable to optimize the stability of the phosphodiester internucleotide linkage and minimize its susceptibility to exonucleases and endonucleases in serum. (Zelphati, O., et al., Antisense. Res. Dev. 3:323-338 [1993]; and Thierry, A. R., et al., pp. 147-161 in Gene Regulation: Biology of Antisense RNA and DNA. Eds. Erickson, R. P. and Izant, J. G., Raven Press, NY [1992]).

Therapeutic nucleic acids being currently being developed do not typically employ the basic phosphodiester chemistry found in natural nucleic acids, because of these and other known problems. Modifications have been made at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. [1997]). Others have attempted to improve stability using 2'-5' sugar linkages (see, e.g., U.S. Pat. No. 5,532,130).

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule.

A single strand siRNA compound may be sufficiently long that it can enter the RISC and participate in RISC mediated cleavage of a target mRNA. A single strand siRNA compound is typically at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

Arrays

A variety of the methods mentioned herein may be adapted for use with arrays that allow sets of mutations to be analyzed and/or detected in a single experiment. For example, biological samples from a subject can be analyzed for the presence of any mutation, including any of the six novel DSTYK mutations described in Table 3, at the same time using a microarray that comprises oligonucleotides that are complementary to each of the mutations. In particular, methods that involve use of oligonucleotide probes are particularly amenable for adaptation to an array-based platform (e.g., microarray). In some embodiments, an array containing multiple probes is known as a mutation panel. See, e.g., Wall et al., "A 31-mutation assay for cystic fibrosis testing in the clinical molecular diagnostics laboratory," Human Mutation, 1995; 5(4):333-8. Other methods may include the use of real-time PCR with probes for detecting DSTYK mutations as described herein.

It will be readily apparent to one skilled in the art that the exact formulation of probes on an array is not critical as long as the user is able to select probes for inclusion on the array that fulfill the function of hybridizing to the targeted mutations/SNPs. The hybridization of a probe complementary to a target oligonucleotide having a DSTYK mutation indicates that the subject from whom the sample was derived is at an elevated risk for developing congenital abnormalities of the kidney and urinary tract ("CAKUT") or confirming a diagnosis of CAKUT.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mm (0.001 inch) to about 20 mm although the thickness of the film is not critical and can be varied over a fairly broad range. Biaxially oriented polypropylene (BOPP) films are also suitable in this regard; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides or proteins onto the support are known to those working in the field; a summary of suitable methods can be found in Matson et al., Anal. Biochem. 217:306-10, 1994. In one example, the oligonucleotides are synthesized onto the support using conventional chemical techniques for preparing oligonucleotides on solid supports (see PCT Publication No. WO 85/01051 and PCT Publication No. WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90 degrees to permit synthesis to proceed within a second (2 degrees) set of rows that are now perpendicular to the first set. This process creates a multiple-channel array whose intersection generates a plurality of discrete cells. In particular examples, the oligonucleotide probes on the array include one or more labels, which permit detection of oligonucleotide probe:target sequence hybridization complexes.

Kits

All the essential materials and reagents required for detecting DSTYK gene and protein mutations in a sample may be assembled together in a kit. This generally will comprise a primer or probe designed to hybridize specifically to or upstream of target nucleotides of the DSTYK gene comprising the mutation of interest. The primer may be labeled with a radioisotope, a fluorophore, a chromophore, a dye, an enzyme, or TOF carrier. Also included may be enzymes suitable for amplifying the target nucleic acids, including various polymerases (reverse transcriptase, Taq, etc.), dNTPs/rNTPs and buffers (e.g., 10× buffer=100 mM Tris-HCl (pH 8.3), and 500 mM KCl) to provide the necessary reaction mixture for amplification. One or more of the deoxynucleotides may be labeled with a radioisotope, a fluorophore, a chromophore, a dye, or an enzyme. Such kits may also include enzymes and other reagents suitable for detection of specific nucleic acids or amplification products.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present embodiment also will typically include a means for packaging the component containers in close confinement for commercial sale. Such packaging may include injection or blow-molded plastic containers into which the desired component containers are retained.

In addition to, or instead of, primers, the kits suitable for determining at least one of the mutations of the DSTYK gene may include the following components: (i) a oligonucleotide probe, usually made of DNA, and that may be pre-labeled. Alternatively, the probe may be unlabeled and the ingredients for labeling may be included in the kit in separate containers; and (ii) hybridization reagents: the kit may also contain other suitably packaged reagents and materials needed for the particular hybridization protocol, including solid-phase matrices, if applicable, and standards.

In another embodiment, the kits may include: (i) sequence determination or amplification primers: sequencing primers may be pre-labeled or may contain an affinity purification or attachment moiety; and (ii) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.

In a particular embodiment, a kit is provided that comprises a pair of nucleotide primers specific for amplifying all or part of the DSTYK gene comprising at least one of the six mutations of Table 3, and oligonucleotides that are complementary to at least one mutation.

Alternatively, the kit of the embodiment may comprise a labeled compound or agent capable of detecting the mutated DSTYK itself (e.g., an antibody or aptamers as described above which binds the wild or mutated DSTYK. For example, the kit may comprise (1) a first antibody (e.g., attached to a solid support) which binds to a polypeptide comprising a mutated protein of Table 3; and, optionally, (2) a second, different antibody which binds to either the polypeptide or the first antibody and is conjugated to a detectable agent.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a bone mineral density related disease.

In one example, the present embodiment includes a diagnostic kit for determining susceptibility to or a risk of developing CAKUT that includes one or more containers, and one or more probes, such as an oligonucleotide probe, capable of binding to one or more DSTYK mutations listed in Table 3. In other embodiments the probe may be selected to allow the DNA to be sequenced to identify new DSTYLK gene mutations (besides those listed in Table 3) as compared to the wild type sequence. The diagnostic kit may be used to detect the binding to a target nucleic acid from a sample by in situ hybridization, PCR, RT-PCR, fluorescence resonance energy transfer, chemiluminescence, enzymatic signal amplification, electron dense particles, magnetic particles, and capacitance coupling. The kit may include those compositions, enzymes and buffers to allow the user to obtain a sample from a patient and have that patient's DNA amplified prior to visualization by direct staining, radiation, chemiluminescence, enzymatic deposition or fluorescence. The probe may be used to detect the target by direct or indirect staining, radiation, chemiluminescence, enzymatic deposition or fluorescence.

These diagnostic kits may comprise one or more reagents that differentiate a normal DSTYK gene or fragment thereof or protein or fragment thereof from a mutant DSTYK gene/fragment or protein/fragment containing one or more mutations selected from Table 3. One or more reagents may comprise one or more nucleic acid probes, or one or more antibodies. One or more reagents may be in the form of a microarray. The kit may further include reagents for primer extension and a control indicative of a healthy individual.

Experimental Materials and Methods

Patients and Controls

Patient recruitment was performed at different research units in Italy (Genoa, Brescia, Parma and Foggia), Macedonia (Skopje), Poland (Poznan, the Polish Registry of Congenital Malformations), Croatia (Split), and New York (Columbia University) after informed consent. The inclusion criteria for enrollment included presence of congenital anomalies of the kidney and urinary tract documented by pre- or post-natal imaging studies such as renal agenesis, renal hypoplasia/dysplasia, duplex kidney, uretero-pelvic junction (UPJ) obstruction, duplicated ureter, vesicoureteral reflux. Available family members were screened to identify familial forms of disease and all patients were investigated for extra-renal manifestations.

One family, K100, was selected for exome sequencing. Analysis of linkage performed yielded signals on chromosomes 1p32-33, 1q25-41, and 6p23-241.[25] A follow-up clinical evaluation of the pedigree was conducted in Sardinia 2009 by a clinical team composed of a pediatric nephrologist and an ultrasonographer to screen all asymptomatic individuals. Clinical data were stored. Seven individuals were confirmed as affected based on documented presence of solitary kidney, renal hypodysplasia, UPJ obstruction or vesicoureteral reflux on imaging studies and fourteen individuals classified as unaffected based on normal abdominal ultrasonography and normal renal function. All other causes of chronic kidney disease with reduced kidney size (such as glomerulonephritis, diabetes mellitus, uncontrolled hypertension) were excluded.

A cohort of 311 patients with congenital kidney and urinary tract malformations recruited from pediatric centers listed above were also screened for independent mutations. The healthy controls with no known history of kidney disease were also recruited from each recruiting center. Moreover, to assess allelic frequency we used publicly available data from dbSNP, 1000 genomes, from the NHLBI GO Exome Sequencing Project (ESP). The Institutional Review Board for Columbia University, and local ethic review committees at collaborating institutions approved our protocol.

DNA Isolation, Genotyping and Analysis of Linkage

Genomic DNA was purified from peripheral blood cells using standard procedures. DNA concentration and purity were tested using a NanoDrop spectrophotometer (Thermo Scientific) and on a 1.5% agarose gel. Genome-wide genotyping for linkage analysis was performed using the Affymetrix 10K 2.0 Chips, which features ~10,000 markers across the genome. Affected-only, multipoint parametric linkage analysis was conducted under an autosomal dominant mode of inheritance, with disease gene frequency=0.001 and phenocopy rate=0.001, using Allegro 2.0 statistical package[26]. PennCNV software[27] was used for CNV analysis using the Illumina 650Y gene chip array (Illumina Inc.) in all affected individuals.

Genotyping and Sequencing

After genome-wide genotyping, affected-only, multipoint parametric linkage analysis was conducted under an autosomal dominant mode of inheritance. Rare copy number variations were excluded using the Illumina 650Y gene chip array. Exome sequencing was performed as previously described[10] in individuals 13 and 20 in K100. We performed Sanger sequencing of DSTYK to validate exome data and search for independent mutations in 311 unrelated CAKUT patients and 384 healthy European controls; of these 96-192 were matched by ethnicity and recruitment site to each patient with a mutation. Self-reported ethnicity was recorded. Coding exons and flanking introns of HNF1B, PAX2, and EYA1 were sequenced in the seven patients carrying DSTYK mutations. Allele frequencies in public databases, Polyphen 2 scores and alignment were determined in 22 mammalian species. Informed consent was obtained from participants and the study was approved by the institutional review boards or ethics committees at all participating sites.

Exome sequencing. Exome sequencing and analysis was performed as previously described[28,29]. Briefly, for each capture experiment, 5 μg of genomic was fragmented, linkers were ligated to the ends and a library was prepared. Genomic DNA was annealed to capture probes, and bound genomic DNA was eluted and subjected to sequencing. Next-Gen sequencing was then performed on an Illumina HiSeq 2000 machine. Sequence reads were converted to FASTQ format and mapped to the reference genome. Reads that aligned to the targeted exome were extracted and statistics on coverage were collected using a Perl script written for this project. Positions found to harbor heterozygous or homozygous variants that deviate from the reference sequence were identified and rare or novel SNPs were identified by comparison to the reference genome, 1000 Genomes data, dbSNP. Low-probability SNVs were identified by empiric methods that we have found significantly reduce false-positive calls: low-quality bases (quality scores <45), heterozygous calls based on low read coverage (<8×), variants that appear exclusively or with high frequency at the same read position on the same strand (implying a preponderance of non-independent reads), and low quality genotype calls using samtools (<40).

Lymphocytes Immortalization and analysis of cDNA. Peripheral blood lymphocytes from members of K100 were EBV immortalized using standard procedures. Total RNA was isolated from 17 lymphoblastoid cell lines, cDNA generated, and Sanger sequencing performed on the cDNA using primers spanning the exons 2 and 3 boundaries.

Validation and search for independent mutations. The reference sequence of DSTYK was downloaded from the National Center for Biotechnology Information (NCBI) database (Build 37.1. NCBI Gene ID Gene ID: 25778, genomic coordinates from GRCh37.p10 Chromosome: 1; NC_000001.10 (205111631 . . . 205180727, corresponding to GenBank No. mRNAs NM_015375.2 and NM_199462.2.

Primers were designed for the 13 coding exons of the gene and amplified PCR products were subjected to direct Sanger sequencing in individuals from K100 and 311 unrelated congenital kidney and urinary tract malformations patients. Sequence traces were analyzed and aligned using Sequencer 4.8 software. All putative pathogenic variants in K100 were confirmed by bidirectional sequencing and tested for segregation in available family members. To filter exome data in K100, variants were sequentially selected based on the following criteria (a) low allele frequency: we eliminated variants present in publicly available databases such as dbSNP, 1000 genomes project and the NHLBI GO Exome Sequencing Project (ESP) (b) damaging effect: we selected nonsense variants, small coding indels, variants affecting the three canonical nucleotides flanking splice junctions; and missense variants that were conserved among 22 mammalian species and predicted to be possibly or probably damaging by Polyphen-2 3[30]) (c) localization to linkage intervals: we selected variants mapping to five intervals defined by linkage analysis. To compare the burden pathogenic variant in DSTYK between congenital kidney and urinary tract malformations patients and EVS population, the following variants were included (1) allele frequency of <0.001 in European and in African Americans (2) nonsense variants, small coding indels, variants affecting the canonical splice sites (3) missense variants that were conserved among 22 mammalian species and predicted to be possibly or probably damaging by Polyphen-2. This yielded 11 damaging missense variant, identified among 14/4300 individuals in EVS database and 7 variants in patients with congenital kidney and urinary tract malformations (1 nonsense, 1 splice site and 3 missense variants in 7 patients). Frequencies were compared by Fisher's exact test.

Sanger sequencing for HNF1B, PAX2, and EYA1. To provide further evidence that the five additional DSTYK mutations identified in seven independent individuals are pathogenic, common genetic causes of congenital kidney and urinary tract malformations in these patients were excluded by direct Sanger sequencing of HNF1B, PAX2, and EYA1. Specific primers were used to direct PCR at each coding exon and products were subjected to bidirectional sequencing. Certain embodiments are directed to the primers below. Primers sequences:

```
                                     (SEQ ID NO: 13)
EYA1-1F_GTC ATT AGC GCA TTA AAT GGT;

(SEQ ID NO: 14)
EYA1-1R_TAC TGA TGA AGA AAC AAG GTG;

(SEQ ID NO: 15)
EYA1-2F_CAC ATC ATG TAG ATT TTG AGA G;

(SEQ ID NO: 16)
EYA1-2R_CAT AAG TAC GTA TAT ACC CAC;

(SEQ ID NO: 17)
EYA1-3F_ATG AAA TTT CCA TCT CCG CAG;

(SEQ ID NO: 18)
EYA1-3R_AAG ATG GAA CAT GTG GGC AC;

(SEQ ID NO: 19)
EYA1-4F_ATC ATG TAG TGG AGA CAC TG;

(SEQ ID NO: 20)
EYA1-4R_TGG GTC TTT AAG TAC CAC TC;

(SEQ ID NO: 21)
EYA1-5F_AAG GGA TAT GTC TTG AAG TG;

(SEQ ID NO: 22)
EYA1-5R_ACT AGA AGC AGG TGT CCT G;

(SEQ ID NO: 23)
EYA1-6F_CAT GAC AAC AGA TTC TAG TG;

(SEQ ID NO: 24)
EYA1-6R_AGC CTT AGG AAA GCT CTC AC;

(SEQ ID NO: 25)
EYA1-7F_GTG AAT TCA GAA AAG GCT CAG;

(SEQ ID NO: 26)
EYA1-7R_TTT AGT CCT TGC CAA AAG CTG;

(SEQ ID NO: 27)
EYA1-8F_AAA CAA GGC TAA TCT TGG CAC;

(SEQ ID NO: 28)
EYA1-8R_CAC TGC TGT TTA CGT AGC AG;

(SEQ ID NO: 29)
EYA1-9F_GTA ATT ATC CTC TTG CAC CTC;

(SEQ ID NO: 30)
EYA1-9R_GGG GTC TGA ATA AGC ATG AC;

(SEQ ID NO: 31)
EYA1-10F_GCC TGC TTC CTC TTA ATG AG;

(SEQ ID NO: 32)
EYA1-10R_CCA ACA AAC CTC TGT CTC AC;

(SEQ ID NO: 33)
EYA1-11-12F_ACT GCC ACC TAC TGA TTG AC;

(SEQ ID NO: 34)
EYA1-11-12R_GTG TGA CAC AAA AGT GTA CAG;

(SEQ ID NO: 35)
EYA1-13F_AGC CGA AGA AAT ATG TTG GTC;

(SEQ ID NO: 36)
EYA1-13R_TCC AAA ATG AAC AAG CAC GAG;

(SEQ ID NO: 37)
EYA1-14F_TCG TGC TTG TTC ATT TTG GAG;

(SEQ ID NO: 38)
EYA1-14R_TCC TGA AGG AAA AGA GCT G;

(SEQ ID NO: 39)
EYA1-15F_TAG TGG GGC ATT CGA ATC AG;

(SEQ ID NO: 40)
EYA1-15R_CAG TGC TTA GAG TAC TGC AC;

(SEQ ID NO: 41)
EYA1-16F_TAT TCT TAG GGG AGG ATT GAG;

(SEQ ID NO: 42)
EYA1-16R_GGA AAT TGC TAA GTT CTG GAG;

(SEQ ID NO: 43)
HNF1B-1-FOR_TAA CAG GTG TCT GGA GGC TG;

(SEQ ID NO: 44)
HNF1B-1-REV_GGC TTG GCG AGT GTG GTC;

(SEQ ID NO: 45)
HNF1B-2-FOR_GGA TGA GGT GTA CCG TAC AG;

(SEQ ID NO: 46)
HNF1B-2-REV_AGT GCT CAC AAG GCC TTG TC;

(SEQ ID NO: 47)
HNF1B-3-FOR_CTG CTG AGT GAA GGC TAC AG;

(SEQ ID NO: 48)
HNF1B-3-REV_GAA GCT CTG ATT TAG CCA CAC;

(SEQ ID NO: 49)
HNF1B-4-FOR_CCA AGA CTG CTG TGA TTG TG;

(SEQ ID NO: 50)
HNF1B-4-REV_AGA TCC GTG GCA AGA ACC AG;

(SEQ ID NO: 51)
HNF1B-5-FOR_CCG AGT CAT TGT TCC AGG AC;

(SEQ ID NO: 52)
HNF1B-5-REV_TTT GAG GCA GGC CTT GTG AG;

(SEQ ID NO: 53)
HNF1B-6-FOR_CAT CGT GTT GGA AAC TGC TC;

(SEQ ID NO: 54)
HNF1B-6-REV_AGT TTG AAG GAG ACC TAC AG;

(SEQ ID NO: 55)
HNF1B-7-FOR_ATC TCC TGT GTA ACA GGC TC;

(SEQ ID NO: 56)
HNF1B-7-REV_ACT TCC GAG AAA GTT CAG AC;

(SEQ ID NO: 57)
HNF1B-8-FOR_TCT ACC TGA GGA GAT GGG AG;

(SEQ ID NO: 58)
HNF1B-8-REV_GCT TGC CAC AAC CTC TGC AC;

(SEQ ID NO: 59)
HNF1B-9-FOR_CTG CAG GAA GTG TGC CTC AG;

(SEQ ID NO: 60)
HNF1B-9-REV_TAA GCA GGG ACC TCT CGC AG;

(SEQ ID NO: 61)
PAX2-1F_CCT CAA GTC CTG AAG TTG AG;
```

-continued

PAX2-1R_GGC AGG TGA TAG GGA TCA G; (SEQ ID NO: 62)

PAX2-2F_CCA CCT TTC TTC TCA AGC TC; (SEQ ID NO: 63)

PAX2-2R_TTC AGC CAC CAT CTG AAC AC; (SEQ ID NO: 64)

PAX2-3F_AAGTCA GCT CAG CCA CAC TG; (SEQ ID NO: 65)

PAX2-3R_TGG ACA AAG AGC AGA GAC TG; (SEQ ID NO: 66)

PAX2-4F_AAT CGC TGA GGA ACT TGG GA; (SEQ ID NO: 67)

PAX2-4R_TTC CTG CCT TTC TCT AGG TG; (SEQ ID NO: 68)

PAX2-5F_CCT TAT GTC CTC TGCTTC TC; (SEQ ID NO: 69)

PAX2-5R_GTC CAA GGA CAA AGC ATG TG; (SEQ ID NO: 70)

PAX2-6F_CTG TGA GGG AAT TGC AGC TC; (SEQ ID NO: 71)

PAX2-6R_TGA GGG CCA GAG GGA ACA T; (SEQ ID NO: 72)

PAX2-7F_TCC TCA GCC AGA TCT CTG AG; (SEQ ID NO: 73)

PAX2-7R_CAA TGC TGG CTA TGC ATG TG; (SEQ ID NO: 74)

PAX2-8F_CGG TTT CAC CAA GTC AGG TC; (SEQ ID NO: 75)

PAX2-8R_TAGAAG CCT CGT TCT CTC TG; (SEQ ID NO: 76)

PAX2-9F_GTA CCC TGG TGT GAG TAG AG; (SEQ ID NO: 77)

PAX2-9R_CAG ACC ATTCAG CAG CTC AC; (SEQ ID NO: 78)

PAX2-9altF_CTG CAA ACC ACT GCT ATT CTG; (SEQ ID NO: 79)

PAX2-9altR_CTG GAA ATG GTTCTT GGC TC; (SEQ ID NO: 80)

PAX2-10F_ATG CCT CCT AGA ACC GGA G; (SEQ ID NO: 81)

PAX2-10R_GTG CTG CAC TAA CAA GCCTG; (SEQ ID NO: 82)

PAX2-11F_TTG TTC TCC TGT TTG TCC TC; and (SEQ ID NO: 83)

PAX2-11R_GGT GAT GTG AAG GGT TGC G. (SEQ ID NO: 84)

Immortalized lymphocytes. Peripheral blood lymphocytes (PBLs) were isolated from blood of members of K100, caring wild-type DSTYK or heterozygous DSTYK mutation, and immortalized with EBV virus using standard procedures. These lymphoblast cell lines (LC) with corresponding DSTYK genotypes were grown in RPMI 1640 medium, supplemented with 10% FBS, 100 U/ml penicillin and 100 ug/ml streptomycin 293T cells were grown in DMEM medium supplemented with 10% FBS, 100 U/ml penicillin and 100 µg/ml streptomycin (all cell culture reagents were from Mediatech). 293T (HEK293T/17) cells were obtained from ATCC.

RNA isolation, cDNA synthesis, quantitative PCR and Sequencing. Total RNA was isolated from 17 lymphocytes cell lines using RNA-Stat-60 (AMS Biotechnology, Abingdon, UK) according to manufacturer's protocol. RNA cleanup was performed using DNaseI (Invitrogen) and the RNeasy mini kit (Qiagen). cDNA was generated using OmniScript RT kit (Qiagen). Sanger sequencing was performed using primers spanning exon-2 (5'-ATCA-GGGCAACTGGGAGAC-3')(SEQ ID NO: 94) and exon-3 (5'-TGTTCCACCAACATGCTCTG-3')(SEQ ID NO: 95) of DSTYK. Expression levels of DSTYK variants were measured by Q-PCR using iQ5 (Bio-Rad) and SYBR Green mix (Clontech). Values were standardized to an internal control reference sample included in each run and GAPDH and BACT were used as a housekeeping control gene (Pfaffl algorithm).

Immunohistochemistry, confocal and electron microscopy. Mouse organs were formalin fixed and paraffin embedded, 3 um sections were cut and used for immunohistochemistry. A kidney and ureter from a pediatric donor (age 3 months) were obtained from International Institute for the Advancement Of Medicine (Edison, N.J.). Immunohistochemistry was performed using the goat anti-RIP5 (Dual serine/threonine and tyrosine protein kinase, DSTYK, UniprotKB: Q6XUX3) antibody (goat, Santa Cruz) and peroxidase-conjugated anti-goat mouse antibody. Mouse organs for immunofluorescence studies were fixed with 4% paraformaldehyde followed by incubation in 30% sucrose in PBS and frozen in Tissue-Tek OCT compound (Sakura Finetek). 5 to 10 um sections were cut and used for staining. Heat-induced antigen retrieval was performed using Target Retrieval Solution (Dako, S-1699) according to manufacturer's instructions. Immunofluorescence was performed using the following antibodies: anti-RIP5 (recognizing the Dual serine/threonine and tyrosine protein kinase, DSTYK, UniprotKB: Q6XUX3; goat, Santa Cruz, sc-162109), anti-FGFR2 (rabbit, Santa Cruz, sc-122), anti-FGFR1 (rabbit, Santa Cruz, sc-121), anti-Aquaporin 2 (rabbit, Sigma-Aldrich, A7310) and anti-Ecadherin (rabbit, BD Biosciences, 610181). Secondary antibodies consisted of Alexa Fluor 488 Donkey Anti-Rabbit and Alexa Fluor 594 Donkey Anti-Goat (Life Technologies A-11058, A-21206), Sections were viewed with a laser-scanning confocal microscope (model LSM 510; Carl Zeiss Inc.).

Zebrafish morpholino knockdown. Wild-type TuAB zebrafish were raised and maintained as previously described[31]. Morpholino oligos (Gene-Tools, Philomath Oreg.) were designed to block the zebrafish dstyk (NM_205627.2) exon 9 splice donor and truncate or delete the ATP binding kinase domain. One cell stage embryos were injected with 4.6 nl of a dstyk exon 9 donor morpholino solution (0.25 or 0.5 mM morpholino in 0.1M KCl/approximately 7-15 ng/embryo) and allowed to develop at 28.5° C. The DSTYK exon 9 antisense morpholino sequence was 5'-ACACTGGCCGTGTACCTTCAGTCCC-3' (SEQ ID NO: 96). Control embryos received the same amount of unrelated scrambled sequence oligo 5'-ACATTTATACTC-CATTCACATGAT-3' (SEQ ID NO: 97). Morpholino injections were also performed in p53 mutant homozygotes (tp53 M214K)[32] to control for non-specific antisense effects. Whole embryo images were obtained on a Leica MZ12 stereomicroscope.

Immunoprecipitation and Western blotting. 293T cells were lysed in the lysis buffer (50 mM tris, pH8.0; 135 mM NaCl, 0.75% NP-40, 1 mM PMSF), supplemented with proteinase inhibitors cocktail Complete (Roche). Protein complex was precipitated overnight using rabbit anti- FGFR2 antibody (Santa Cruz) or rabbit IgG control (Invitrogen) and Dynabeads Protein G (Invitrogen). The precipitated complexes were boiled in Laemmli buffer, separated in 7.5% PAGE and transferred onto nitrocellulose membrane. Detection of proteins of interest was performed using Immobilon Western ECL detection kit (Millipore) and the following antibodies:goat anti-RIP5 (Dual serine/threonine and tyrosine protein kinase, DSTYK, UniprotKB: Q6XUX3) and rabbit anti-FGFR2 antibody (Santa Cruz), mouse anti-rabbit IgG (conformation specific) antibody (L27A9) (Cell signaling) and HRP labeled donkey anti-goat antibody (Santa-Cruz) or donkey anti-rabbit antibody (Jackson ImmunoResearch).

siRNA Knockdown. 293T cells were transfected with smartpool DSTYK (mixture of four siRNA duplexes selected and custom designed to target DSTYK; Thermo Scientific) or control negative pool siRNA (Dharmacon) using Lipofectamine 2000 (Invitrogen). Quantitative PCR (qPCR) analysis of DSTYK transcript levels was performed at 48 hours post transfection and showed up to 82% reduction in DSTYK levels by DSTYK siRNA compared to no effect in cells transfected with control negative pool. At 72-96 h post transfection the cells were starved in serum-free medium for 18 hours and treated with 100 ng/ml basic FGF for 15 min. The cells were harvested, lysed in Laemmli buffer and subjected to western blotting. Cell lysates were separated in 10% SDSPAGE and transferred onto nitrocellulose membrane. Detection of proteins of interest was performed using the following antibodies: goat anti-RIP5 (Dual serine/threonine and tyrosine protein kinase, DSTYK, UniprotKB: Q6XUX3) and rabbit anti-FGFR2 antibody (Santa Cruz), mouse anti-GAPDH (R&D Systems), rabbit antipERK1/2 and anti-ERK1/2 (Cell signaling) and HRP labeled sheep anti-mouse (Amersham), donkey anti-goat antibody (Santa-Cruz) or donkey anti-rabbit (Jackson ImmunoResearch). All experiments were confirmed in at least three independent reactions.

Heterozygous Mutations in DSTYK Cause Autosomal Dominant Congenital Abnormalities of the Kidney and Urinary Tract Sequence analysis of DSTYK cDNA from lymphobastoid cell lines in seventeen pedigree members demonstrated that all mutation carriers harbor a heterozygous 27 bp deletion resulting from use of an alternative splice donor within the normal exon 2, which would produce a nine amino acid in-frame deletion (VTMHHALLQ, SEQ ID NO: 7) in a domain that is highly conserved among mammals.

Independent mutations in DSTYK in 311 additional CAKUT patients were investigated. A nonsense mutation (p.W8X) was identified in a patient with UPJO and early-onset ataxia, and a splice site mutation (c.655-3 C>T) in two siblings affected by UPJO. Five other individuals were identified who harbored three missense variants that occur at completely conserved positions in mammals and were predicted to be damaging by Polyphen 2 (p.R29Q, p.D200G, and p.S843L). These five damaging variants were absent in all public databases and were also not detected in 384 healthy European controls. Moreover, none of these patients carried deleterious structural variants[12] or point mutations in HNF1B, PAX2, or EYA1. The phenotypic spectrum associated with DSTYK mutations is described above in Table 3.

In summary, in addition to the splice site mutation in K100, five novel damaging DSTYK variants were identified in 7 of 311 unrelated CAKUT patients (2.2%). As a comparison, the NHBLI exome variant server (EVS, a database which contains exome data in 6,503 individuals) does not contain any DSTYK nonsense mutations or variants affecting the 3 canonical nucleotides flanking splice junctions. Only 0.3% of Caucasian individuals in the EVS database harbor rare damaging DSTYK missense variants affecting completely conserved positions in mammals, indicating a significant excess burden of rare damaging variants among CAKUT cases (11 damaging missense variants with minor allele frequency <0.001 were detected in 14/4300 Caucasian individuals in the EVS database vs. 7/311 CAKUT patients, OR=7.1, Fisher exact p-value=$3 \times 10^{-4}$).

DSTYK is Ubiquitously Expressed and Localizes to Cell Membranes of Major Organs

DSTYK has a striking membrane-associated distribution in mesenchymal-derived cells of all major organs. In the developing mouse kidney, it is expressed at low levels in the nephrogenic zone and but is more highly expressed in maturing tubular epithelia, with the most prominent expression in the medulla and the papilla. In the postnatal mouse and human pediatric kidney, DSTYK is detected in the basolateral and apical membranes of all tubular epithelia. It has a very prominent basolateral and cytoplasmic distribution in the thin ascending limb of the loop of Henle and the distal convoluted tubule, and a distribution restricted to apical and basolateral membranes in the collecting duct. DSTYK is expressed in both principal and intercalated cells of the collecting duct. DSTYK was also detected in all layers of transitional ureteric epithelium and in the ureteric smooth muscle cells.

Morpholino Knock-down in Zebrafish Results in Multi-organ Developmental Defects

To investigate the role of DSTYK in embryonic development, knockdown experiments were performed of the ortholog in zebrafish. With maximal knockdown, embryos showed growth retardation as evidenced by small fins, abnormal tail morphogenesis and loss of heartbeat. Cloacal malformations were also observed which correspond to lower genitourinary defects in mammals and defects in jaw development, as well as specific loss of the median fin fold. Pericardial effusion was evident in day-5 morphant larvae, which was attributable to both heart and kidney failure. These data suggest an essential role of DSTYK in the development of major organs. Of note, these developmental defects resemble phenotypes produced by global loss of FGF signaling in zebrafish[13-15].

DSTYK Colocalizes with Fibroblast Growth Factor (FGF) Receptors in Developing and Adult Kidney and Mediates FGF Signaling In the developing nephron (E12.5), DSTYK colocalizes with E-Cadherin positive and negative cells, confirming that is expressed both in the metanephric mesenchyme (MM) and the ureteric bud (UB). DSTYK localization to cell membrane in the MM and UB highly parallels the known expression pattern of Fibroblast Growth Factor (FGF) receptors. Consistent with this prediction, DSTYK colocalizes with both FGFR1 and FGFR2 in the UB and comma-shaped bodies. Co-localization with FGFR2 was also evident in distal tubular cells in the adult renal medulla and papilla. Punctate DSTYK staining was seen at apical cell-cell junctions lining ureteric bud epithelia. Upon activation, FGF receptors trigger cytoplasmic protein kinases, resulting in phosphorylation of extracellular-signal-regulated kinase (ERK), which is the main effector of FGF-induced transcriptional activity[16,17]. Because DSTYK encodes a kinase and colocalizes with FGFR1 and FGFR2, it is hypothesized that DSTYK acts as a positive regulator of FGF-mediated signaling in the kidney. To test this hypothesis, siRNA knockdown of DSTYK was performed, which resulted in up to 80% reduction of transcript levels and pronounced reduction of DSTYK protein levels by 96 hours post-transfection. FGF stimulation augmented diphospho-ERK levels as expected, but siRNA silencing of DSTYK significantly prevented ERK phosphorylation. This effect was not mediated by a direct physical interaction of DSTYK with FGFR2. Combined with co-localization of DSTYK with FGFR1 and FGFR2, these data implicate DSTYK downstream of FGF signaling.

Embodiments illustrated herein by the experiments described above and by the examples, should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

REFERENCES

1. Loane M, Dolk H, Kelly A, Teljeur C, Greenlees R, Densem J. Paper 4: EUROCAT statistical monitoring: identification and investigation of ten year trends of congenital anomalies in Europe. Birth Defects Res A Clin Mol Teratol 2011; 91 Suppl 1:S31-43.
2. Birth Defects Monitoring Program (BDMP)/Commission on Professional and Hospital Activities (CPHA) surveillance data, 1988-1991. Teratology 1993; 48:658-75.
3. Ardissino G, Dacco V, Testa S, et al. Epidemiology of chronic renal failure in children: data from the ItalKid project. Pediatrics 2003; 111:e382-7.
4. Sanna-Cherchi S, Ravani P, Corbani V, et al. Renal outcome in patients with congenital anomalies of the kidney and urinary tract. Kidney Int 2009; 76:528-33.
5. Woolf A S, Winyard P J. Molecular mechanisms of human embryogenesis: developmental pathogenesis of renal tract malformations. Pediatr Dev Pathol 2002; 5:108-29.
6. Weber S, Moriniere V, Knuppel T, et al. Prevalence of mutations in renal developmental genes in children with renal hypodysplasia: results of the ESCAPE study. J Am Soc Nephrol 2006; 17:2864-70.
7. Thomas R, Sanna-Cherchi S, Warady B A, Furth S L, Kaskel F J, Gharavi A G. HNF1B and PAX2 mutations are a common cause of renal hypodysplasia in the CKiD cohort. Pediatr Nephrol 2011; 26:897-903.
8. Sanna-Cherchi S, Caridi G, Weng P L, et al. Localization of a Gene for Nonsyndromic Renal Hypodysplasia to Chromosome 1p32-33. In: Am J Hum Genet; 2007:539-49.
9. Weng P L, Sanna-Cherchi S, Hensle T, et al. A recessive gene for primary vesicoureteral reflux maps to chromosome 12p11-q13. J Am Soc Nephrol 2009; 20:1633-40.
10. Boyden L M, Choi M, Choate K A, et al. Mutations in kelch-like 3 and cullin 3 cause hypertension and electrolyte abnormalities. Nature 2012; 482:98-102.
11. Langenau D M, Feng H, Berghmans S, Kanki J P, Kutok J L, Look A T. Cre/lox-regulated transgenic zebrafish model with conditional myc-induced T cell acute lymphoblastic leukemia. Proceedings of the National Academy of Sciences of the United States of America 2005; 102:6068-73.
12. Sanna-Cherchi S, Kiryluk K, Burgess K E, et al. Copy-number disorders are a common cause of congenital kidney malformations. Am J Hum Genet 2012; 91:987-97.
13. Abe G, Ide H, Tamura K. Function of FGF signaling in the developmental process of the median fin fold in zebrafish. Dev Biol 2007; 304:355-66.
14. Griffin K J, Kimelman D. Interplay between FGF, one-eyed pinhead, and T-box transcription factors during zebrafish posterior development. Dev Biol 2003; 264: 456-66.
15. Nissen R M, Yan J, Amsterdam A, Hopkins N, Burgess S M. Zebrafish foxi one modulates cellular responses to Fgf signaling required for the integrity of ear and jaw patterning. Development 2003; 130:2543-54.
16. Bates C M. Role of fibroblast growth factor receptor signaling in kidney development. American journal of physiology Renal physiology 2011; 301:F245-51.
17. Corson L B, Yamanaka Y, Lai K M, Rossant J. Spatial and temporal patterns of ERK signaling during mouse embryogenesis. Development 2003; 130:4527-37.
18. Schedl A. Renal abnormalities and their developmental origin. Nat Rev Genet 2007; 8:791-802.
19. Sanna-Cherchi S, Caridi G, Weng P L, et al. Genetic approaches to human renal agenesis/hypoplasia and dysplasia. Pediatr Nephrol 2007; 22:1675-84.
20. Guillemot F, Zimmer C. From cradle to grave: the multiple roles of fibroblast growth factors in neural development. Neuron 2011; 71:574-88.
21. Barak H, Huh S H, Chen S, et al. FGF9 and FGF20 maintain the stemness of nephron progenitors in mice and man. Developmental cell 2012; 22:1191-207.
22. Poladia D P, Kish K, Kutay B, et al. Role of fibroblast growth factor receptors 1 and 2 in the metanephric mesenchyme. Developmental biology 2006; 291:325-39.
23. Zhao H, Kegg H, Grady S, et al. Role of fibroblast growth factor receptors 1 and 2 in the ureteric bud. Developmental biology 2004; 276:403-15.
24. Zha J, Zhou Q, Xu L G, et al. RIP5 is a RIP-homologous inducer of cell death. Biochemical and biophysical research communications 2004; 319:298-303.
25. Sanna-Cherchi S, Caridi G, Weng P L, et al. Localization of a Gene for Nonsyndromic Renal Hypodysplasia t Chromosome 1p32-33. In: Am J Hum Genet; 2007: 539-49.
26. Gudbjartsson D F, Jonasson K, Frigge M L, Kong A. Allegro, a new computer program for multipoint linkage analysis. Nat Genet 2000; 25: 12-3.
27. Wang K, Li M, Hadley D, et al. Penn C N V: an integrated hidden Markov model designed for high-resolution copy number variation detection in whole-genome SNP genotyping data. Genome Res 2007; 17: 1665-74.
28. Boyden L M, Choi M, Choate K A, et al. Mutations in kelch-like 3 and cullin 3 cause hypertension and electrolyte abnormalities. Nature 2012; 482: 98-102.
29. Sanna-Cherchi S, Burgess K E, Nees S N, et al. Exome sequencing identified MYO1E and NEIL1 as candidate genes for human autosomal recessive steroid-resistant nephrotic syndrome. Kidney Int 2011; 80: 389-96.
30. Adzhubei I A, Schmidt S, Peshkin L, et al. A method and server for predicting damaging missens mutations. Nat Methods 2010; 7: 248-9.
31. Westerfield M. The zebrafish book. A guide for the laboratory use of zebrafish (*Danio rerio*). Eugen, Oreg.: Univ. of Oregon Press; 2000.
32. Langenau D M, Feng H, Berghmans S, Kanki J P, Kutok J L, Look A T. Cre/lox-regulated transgenic zebrafish model with conditional myc-induced T cell acute lymphoblastic leukemia. Proc Natl Acad Sci USA 2005; 102: 6068-73.

What is claimed is:

1. A method for treating cancer in a subject comprising introducing siRNA that hybridizes specifically to target nucleotides of the dual serine/threonine and tyrosine protein kinase (DSTYK) gene, wherein the cancer is selected from the group consisting of: lung cancer, endometrial cancer, estrogen receptor (ER)-positive breast cancer, diffuse-type gastric cancer, triple-negative breast cancer, 8p11 myeloproliferative syndrome, alveolar rhabdomyosarcoma, peripheral T-cell lymphoma, glioblastoma multiforme, endometrial uterine cancer and melanoma, invasive bladder tumors, and rhabdomyosarcoma.

2. The method of claim 1, wherein the subject has been determined to harbor a dual serine/threonine and tyrosine protein kinase (DSTYK) mutation.

* * * * *